United States Patent
Askem

(10) Patent No.: US 9,901,664 B2
(45) Date of Patent: Feb. 27, 2018

(54) CONTROLLING OPERATION OF A REDUCED PRESSURE THERAPY SYSTEM BASED ON DYNAMIC DUTY CYCLE THRESHOLD DETERMINATION

(71) Applicant: SMITH & NEPHEW PLC, London (GB)

(72) Inventor: Ben Alan Askem, Brough (GB)

(73) Assignee: SMITH & NEPHEW PLC, London (GB)

( * ) Notice: Subject to any disclaimer, the term of this patent is extended or adjusted under 35 U.S.C. 154(b) by 796 days.

(21) Appl. No.: 14/386,322

(22) PCT Filed: Mar. 13, 2013

(86) PCT No.: PCT/IB2013/000866
§ 371 (c)(1),
(2) Date: Sep. 18, 2014

(87) PCT Pub. No.: WO2013/140255
PCT Pub. Date: Sep. 26, 2013

(65) Prior Publication Data
US 2015/0051560 A1 Feb. 19, 2015

Related U.S. Application Data

(60) Provisional application No. 61/613,456, filed on Mar. 20, 2012.

(51) Int. Cl.
*A61M 1/00* (2006.01)
*A61M 27/00* (2006.01)
*H02M 1/00* (2006.01)

(52) U.S. Cl.
CPC ........ *A61M 1/0037* (2013.01); *A61M 1/0031* (2013.01); *A61M 1/0088* (2013.01);
(Continued)

(58) Field of Classification Search
CPC .............. A61M 1/0031; A61M 1/0088; A61M 1/0037; A61M 2205/276;
(Continued)

(56) References Cited

U.S. PATENT DOCUMENTS 3,972,328 A 8/1976 Chen
4,029,598 A 6/1977 Neisius et al.
(Continued)

FOREIGN PATENT DOCUMENTS

CN 101940805 A 1/2011
DE 34 43 101 5/1986
(Continued)

OTHER PUBLICATIONS

PCT Search Report and Written Opinion for International Application No. PCT/IB2013/000866, dated Jul. 29, 2013 in 11 pages.
(Continued)

*Primary Examiner* — Adam Marcetich
(74) *Attorney, Agent, or Firm* — Knobbe, Martens, Olson & Bear LLP

(57) ABSTRACT

Negative pressure wound therapy apparatuses and dressings, and systems and methods for operating such apparatuses for use with dressings are disclosed. In some embodiments, controlling the delivery of therapy can be based on monitoring and detecting various operating conditions. An apparatus can have a controller configured to monitor a duty cycle of a source of negative pressure. Based on the monitored duty cycle, the controller can determine whether a leak is present and provide an indication to a user. The controller can determine a duty cycle threshold in order to achieve an optimal or near optimal balance between an uninterrupted delivery of therapy, avoidance inconveniencing a user, conserving power, achieving optimal or near optimal efficiency, and/or limiting vibrational noise. In some embodiments, the
(Continued)

duty cycle threshold is determined based at least in part on a capacity of a power source and an operational time of the apparatus.

28 Claims, 13 Drawing Sheets

(52) U.S. Cl.
CPC ... *A61M 2205/15* (2013.01); *A61M 2205/276* (2013.01); *A61M 2209/088* (2013.01); *H02M 2001/0003* (2013.01); *H02M 2001/0012* (2013.01)

(58) Field of Classification Search
CPC ........ A61M 2209/088; A61M 2205/15; A61M 2205/8206; A61M 2205/8212; A61M 2205/18; A61M 1/0066; H02M 3/157; H02M 3/33515
See application file for complete search history.

(56) References Cited

U.S. PATENT DOCUMENTS

| | | |
|---|---|---|
| 4,502,842 A | 3/1985 | Currier et al. |
| 4,813,942 A | 3/1989 | Alvarez |
| 5,056,510 A | 10/1991 | Gilman |
| 5,181,905 A | 1/1993 | Flam |
| 5,222,714 A | 6/1993 | Morinigo et al. |
| 5,238,732 A | 8/1993 | Krishnan |
| 5,291,822 A | 3/1994 | Alsobrooks et al. |
| 5,349,896 A | 9/1994 | Connelly et al. |
| 5,358,494 A | 10/1994 | Svedman |
| 5,417,743 A | 5/1995 | Dauber |
| 5,449,003 A | 9/1995 | Sugimura |
| 5,449,347 A | 9/1995 | Preen et al. |
| 5,466,229 A | 11/1995 | Elson |
| 5,549,584 A | 8/1996 | Gross |
| 5,634,391 A | 6/1997 | Eady |
| 5,676,525 A | 10/1997 | Berner et al. |
| 5,687,633 A | 11/1997 | Eady |
| 5,693,013 A | 12/1997 | Geuder |
| 5,707,499 A | 1/1998 | Joshi et al. |
| 5,730,587 A | 3/1998 | Snyder et al. |
| 5,743,170 A | 4/1998 | Forman et al. |
| 5,759,570 A | 6/1998 | Arnold |
| 5,769,608 A | 6/1998 | Seale |
| 5,772,403 A | 6/1998 | Allison et al. |
| 5,785,508 A | 7/1998 | Bolt |
| 5,863,184 A | 1/1999 | Juterbock et al. |
| 5,897,296 A | 4/1999 | Yamamoto et al. |
| 5,950,523 A | 9/1999 | Reynolds |
| 6,068,588 A | 5/2000 | Goldowsky |
| 6,071,267 A | 6/2000 | Zamierowski |
| 6,080,685 A | 6/2000 | Eady |
| 6,102,680 A | 8/2000 | Fraser et al. |
| 6,138,550 A | 10/2000 | Fingar, Jr. |
| 6,145,430 A | 11/2000 | Able et al. |
| 6,158,327 A | 12/2000 | Huss |
| 6,162,194 A | 12/2000 | Shipp |
| 6,227,825 B1 | 5/2001 | Vay |
| 6,230,609 B1 | 5/2001 | Fingar |
| 6,231,310 B1 | 5/2001 | Tojo et al. |
| 6,249,198 B1 | 6/2001 | Clark et al. |
| 6,323,568 B1 | 11/2001 | Zabar |
| 6,327,960 B1 | 12/2001 | Heimueller et al. |
| 6,343,539 B1 | 2/2002 | Du |
| 6,413,057 B1 | 7/2002 | Hong et al. |
| 6,540,490 B1 | 4/2003 | Lilie |
| 6,589,028 B1 | 7/2003 | Eckerbom et al. |
| 6,626,891 B2 | 9/2003 | Ohmstede |
| 6,638,035 B1 | 10/2003 | Puff |
| 6,655,257 B1 | 12/2003 | Meyer |
| 6,673,036 B1 | 1/2004 | Britto |
| 6,685,681 B2 | 2/2004 | Lockwood et al. |
| 6,752,794 B2 | 6/2004 | Lockwood et al. |
| 6,776,769 B2 | 8/2004 | Smith |
| 6,823,905 B1 | 11/2004 | Smith et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,041,057 B1 | 5/2006 | Faupel et al. |
| 7,070,584 B2 | 7/2006 | Johnson et al. |
| 7,108,683 B2 | 9/2006 | Zamierowski |
| 7,128,735 B2 | 10/2006 | Weston |
| 7,151,348 B1 | 12/2006 | Ueda et al. |
| 7,216,651 B2 | 5/2007 | Argenta et al. |
| 7,361,184 B2 | 4/2008 | Joshi |
| 7,381,859 B2 | 6/2008 | Hunt et al. |
| 7,447,327 B2 | 11/2008 | Kitamura et al. |
| 7,553,306 B1 | 6/2009 | Hunt et al. |
| 7,569,742 B2 | 8/2009 | Haggstrom et al. |
| 7,605,298 B2 | 10/2009 | Bechert et al. |
| 7,615,036 B2 | 11/2009 | Joshi et al. |
| 7,622,629 B2 | 11/2009 | Aail |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,708,724 B2 | 5/2010 | Weston |
| 7,722,582 B2 | 5/2010 | Lina et al. |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| 8,034,037 B2 | 10/2011 | Adams et al. |
| 8,062,272 B2 | 11/2011 | Weston |
| 8,062,331 B2 | 11/2011 | Zamierowski |
| 8,080,702 B2 | 12/2011 | Blott et al. |
| 8,118,794 B2 | 2/2012 | Weston et al. |
| 8,152,785 B2 | 4/2012 | Vitaris |
| 8,162,907 B2 | 4/2012 | Heagle |
| 8,192,409 B2 | 6/2012 | Hardman et al. |
| 8,207,392 B2 | 6/2012 | Haggstrom et al. |
| 8,235,972 B2 | 8/2012 | Adahan |
| 8,241,015 B2 | 8/2012 | Lillie |
| 8,241,261 B2 | 8/2012 | Randolph et al. |
| 8,257,328 B2 | 9/2012 | Augustine et al. |
| 8,267,918 B2 | 9/2012 | Johnson et al. |
| 8,282,611 B2 | 10/2012 | Weston |
| 8,303,552 B2 | 11/2012 | Weston |
| 8,323,264 B2 | 12/2012 | Weston et al. |
| 8,372,050 B2 | 2/2013 | Jaeb et al. |
| 8,425,478 B2 | 4/2013 | Olson |
| 8,444,612 B2 | 5/2013 | Patel et al. |
| 8,460,255 B2 | 6/2013 | Joshi et al. |
| 8,535,296 B2 | 9/2013 | Blott et al. |
| 8,540,688 B2 | 9/2013 | Eckstein et al. |
| 8,545,466 B2 | 10/2013 | Andresen et al. |
| 8,568,386 B2 | 10/2013 | Malhi |
| 8,617,129 B2 | 12/2013 | Hartwell |
| 8,622,981 B2 | 1/2014 | Hartwell et al. |
| 8,628,505 B2 | 1/2014 | Weston |
| 8,641,691 B2 | 2/2014 | Fink |
| 8,663,198 B2 | 3/2014 | Buan et al. |
| 8,715,256 B2 | 5/2014 | Greener |
| 8,764,732 B2 | 7/2014 | Hartwell |
| 8,791,316 B2 | 7/2014 | Greener |
| 8,795,243 B2 | 8/2014 | Weston |
| 8,808,274 B2 | 8/2014 | Hartwell |
| 8,827,983 B2 | 9/2014 | Braga et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |

(56) References Cited

U.S. PATENT DOCUMENTS

| | | |
|---|---|---|
| 8,905,985 B2 | 12/2014 | Hull et al. |
| 8,945,074 B2 | 2/2015 | Buan et al. |
| 8,951,235 B2 | 2/2015 | Allen et al. |
| 8,956,336 B2 | 2/2015 | Haggstrom et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,127,665 B2 | 9/2015 | Locke et al. |
| 9,168,330 B2 | 10/2015 | Joshi et al. |
| 9,199,012 B2 | 12/2015 | Vitaris et al. |
| 9,283,118 B2 | 3/2016 | Locke et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,446,178 B2 | 9/2016 | Blott et al. |
| 9,452,248 B2 | 9/2016 | Blott et al. |
| 9,506,463 B2 | 11/2016 | Locke et al. |
| 9,518,575 B2 | 12/2016 | Felber |
| 9,669,138 B2 | 6/2017 | Joshi et al. |
| 2001/0001278 A1 | 5/2001 | Drevet |
| 2001/0033795 A1 | 10/2001 | Humpheries |
| 2001/0043870 A1 | 11/2001 | Song |
| 2002/0026946 A1 | 3/2002 | McKay |
| 2002/0122732 A1 | 9/2002 | Oh et al. |
| 2002/0161317 A1 | 10/2002 | Risk et al. |
| 2002/0164255 A1 | 11/2002 | Burr et al. |
| 2003/0035743 A1 | 2/2003 | Lee et al. |
| 2003/0040687 A1 | 2/2003 | Boynton et al. |
| 2003/0095879 A1 | 5/2003 | Oh et al. |
| 2003/0099558 A1 | 5/2003 | Chang |
| 2003/0108430 A1 | 6/2003 | Yoshida et al. |
| 2003/0110939 A1 | 6/2003 | Able et al. |
| 2003/0133812 A1 | 7/2003 | Puff et al. |
| 2003/0161735 A1 | 8/2003 | Kim et al. |
| 2003/0168990 A1* | 9/2003 | Schenk ............ H05B 39/047 315/82 |
| 2003/0175125 A1 | 9/2003 | Kwon et al. |
| 2003/0175135 A1 | 9/2003 | Heo et al. |
| 2003/0230191 A1 | 12/2003 | Ohrle et al. |
| 2004/0005222 A1 | 1/2004 | Yoshida et al. |
| 2004/0066097 A1 | 4/2004 | Kobayashi et al. |
| 2004/0071568 A1 | 4/2004 | Hyeon |
| 2004/0071572 A1 | 4/2004 | Greter et al. |
| 2004/0115076 A1 | 6/2004 | Lilie et al. |
| 2004/0118460 A1 | 6/2004 | Stinson |
| 2004/0126250 A1 | 7/2004 | Tsuchiya et al. |
| 2004/0156730 A1 | 8/2004 | Lilie et al. |
| 2004/0163713 A1 | 8/2004 | Schulze et al. |
| 2004/0182237 A1 | 9/2004 | Headley et al. |
| 2004/0189103 A1 | 9/2004 | Duncan et al. |
| 2005/0031470 A1 | 2/2005 | Lee |
| 2005/0098031 A1 | 5/2005 | Yoon et al. |
| 2005/0110190 A1 | 5/2005 | Giardini |
| 2005/0111987 A1 | 5/2005 | Yoo et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0135946 A1 | 6/2005 | Kang et al. |
| 2005/0142007 A1 | 6/2005 | Lee et al. |
| 2005/0142008 A1 | 6/2005 | Jung et al. |
| 2005/0155657 A1 | 7/2005 | Kack et al. |
| 2005/0163635 A1 | 7/2005 | Berwanger et al. |
| 2005/0209560 A1 | 9/2005 | Boukhny et al. |
| 2005/0251117 A1 | 11/2005 | Anderson et al. |
| 2005/0271526 A1 | 12/2005 | Chang et al. |
| 2005/0272142 A1 | 12/2005 | Horita |
| 2005/0276706 A1 | 12/2005 | Radue |
| 2006/0009744 A1 | 1/2006 | Edrman et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0029675 A1 | 2/2006 | Ginther |
| 2006/0039806 A1 | 2/2006 | Becker |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0073036 A1 | 4/2006 | Debrito et al. |
| 2006/0083623 A1 | 4/2006 | Higgins et al. |
| 2006/0110259 A1 | 5/2006 | Puff et al. |
| 2006/0118190 A1 | 6/2006 | Takehana et al. |
| 2006/0122558 A1 | 6/2006 | Sherman et al. |
| 2006/0191575 A1 | 8/2006 | Naesje |
| 2006/0192259 A1 | 8/2006 | Silverbrook |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0282174 A1 | 12/2006 | Haines |
| 2006/0287632 A1 | 12/2006 | Sarangapani |
| 2007/0016152 A1 | 1/2007 | Karpowicz et al. |
| 2007/0032741 A1 | 2/2007 | Hibner et al. |
| 2007/0041856 A1 | 2/2007 | Hansen et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0179460 A1 | 8/2007 | Adahan |
| 2007/0196214 A1 | 8/2007 | Bocchiola |
| 2007/0225663 A1 | 9/2007 | Watt et al. |
| 2007/0256428 A1 | 11/2007 | Unger et al. |
| 2007/0260226 A1 | 11/2007 | Jaeb et al. |
| 2007/0282283 A1 | 12/2007 | Kaern et al. |
| 2007/0295201 A1 | 12/2007 | Dadd |
| 2008/0004549 A1* | 1/2008 | Anderson ............ A61M 1/0023 601/6 |
| 2008/0015526 A1 | 1/2008 | Reiner et al. |
| 2008/0020178 A1 | 1/2008 | Oehrle et al. |
| 2008/0051708 A1 | 2/2008 | Kumar et al. |
| 2008/0071234 A1 | 3/2008 | Kelch et al. |
| 2008/0071235 A1 | 3/2008 | Locke et al. |
| 2008/0082040 A1 | 4/2008 | Kubler et al. |
| 2008/0094753 A1 | 4/2008 | Brodkin et al. |
| 2008/0110336 A1 | 5/2008 | Bovill et al. |
| 2008/0125697 A1 | 5/2008 | Gao |
| 2008/0125698 A1 | 5/2008 | Gerg et al. |
| 2008/0132821 A1 | 6/2008 | Propp et al. |
| 2008/0162968 A1* | 7/2008 | Breen .................. G06F 1/3203 713/323 |
| 2008/0211435 A1 | 9/2008 | Imagawa |
| 2008/0234641 A1 | 9/2008 | Locke et al. |
| 2008/0240942 A1 | 10/2008 | Heinrich et al. |
| 2008/0260551 A1 | 10/2008 | Simmons |
| 2008/0281281 A1 | 11/2008 | Meyer et al. |
| 2008/0306456 A1 | 12/2008 | Riesinger |
| 2008/0310980 A1 | 12/2008 | Ramsdorf et al. |
| 2009/0027025 A1* | 1/2009 | Latham ................ H02M 3/157 323/283 |
| 2009/0028733 A1 | 1/2009 | Duwel |
| 2009/0053081 A1 | 2/2009 | Griffiths |
| 2009/0071551 A1 | 3/2009 | Chalich |
| 2009/0079571 A1* | 3/2009 | Calvarese ............ G06K 7/0008 340/572.4 |
| 2009/0081049 A1 | 3/2009 | Tian et al. |
| 2009/0087323 A1 | 4/2009 | Blakey et al. |
| 2009/0114293 A1 | 5/2009 | Kanai et al. |
| 2009/0125004 A1 | 5/2009 | Shen et al. |
| 2009/0129986 A1 | 5/2009 | Wimberger-Friedl et al. |
| 2009/0149821 A1 | 6/2009 | Scherson et al. |
| 2009/0157024 A1 | 6/2009 | Song |
| 2009/0166411 A1 | 7/2009 | Kramer et al. |
| 2009/0206778 A1 | 8/2009 | Roh et al. |
| 2009/0227969 A1 | 9/2009 | Jaeb et al. |
| 2009/0234306 A1 | 9/2009 | Vitaris |
| 2009/0273349 A1* | 11/2009 | Rondoni .............. A61N 1/3708 324/430 |
| 2009/0299251 A1 | 12/2009 | Buan |
| 2009/0299306 A1 | 12/2009 | Buan |
| 2009/0304534 A1 | 12/2009 | Richter |
| 2010/0042059 A1 | 2/2010 | Pratt et al. |

(56) References Cited

U.S. PATENT DOCUMENTS

| | | | |
|---|---|---|---|
| 2010/0045215 A1* | 2/2010 | Hawker | A47L 5/24 318/139 |
| 2010/0068820 A1 | 3/2010 | Meathrel et al. | |
| 2010/0098566 A1 | 4/2010 | Kang | |
| 2010/0125258 A1 | 5/2010 | Coulthard et al. | |
| 2010/0145289 A1 | 6/2010 | Line et al. | |
| 2010/0191178 A1 | 7/2010 | Ross et al. | |
| 2010/0204663 A1 | 8/2010 | Wudyka | |
| 2010/0207768 A1 | 8/2010 | Pidgeon | |
| 2010/0211030 A1 | 8/2010 | Turner et al. | |
| 2010/0222847 A1* | 9/2010 | Goetz | A61M 5/14276 607/60 |
| 2010/0244780 A1 | 9/2010 | Turner | |
| 2010/0265649 A1 | 10/2010 | Singh et al. | |
| 2010/0268179 A1 | 10/2010 | Kelch et al. | |
| 2010/0280435 A1 | 11/2010 | Raney et al. | |
| 2010/0305526 A1 | 12/2010 | Robinson et al. | |
| 2010/0318052 A1 | 12/2010 | Ha et al. | |
| 2010/0318071 A1 | 12/2010 | Wudyka | |
| 2010/0328933 A1* | 12/2010 | Maldonado | F21S 9/035 362/183 |
| 2011/0000069 A1 | 1/2011 | Ramsdorf et al. | |
| 2011/0004172 A1 | 1/2011 | Eckstein et al. | |
| 2011/0015587 A1 | 1/2011 | Tumey et al. | |
| 2011/0015619 A1* | 1/2011 | Svedman | A61L 15/60 604/543 |
| 2011/0020588 A1 | 1/2011 | Kinugawa et al. | |
| 2011/0038741 A1 | 2/2011 | Lissner et al. | |
| 2011/0071415 A1 | 3/2011 | Karwoski et al. | |
| 2011/0081267 A1 | 4/2011 | McCrone et al. | |
| 2011/0092958 A1 | 4/2011 | Jacobs | |
| 2011/0098600 A1 | 4/2011 | Matsumura et al. | |
| 2011/0103984 A1 | 5/2011 | Santa | |
| 2011/0118683 A1 | 5/2011 | Weston | |
| 2011/0171044 A1 | 7/2011 | Flanigan | |
| 2011/0176945 A1 | 7/2011 | Drevet | |
| 2011/0176946 A1 | 7/2011 | Drevet | |
| 2011/0224631 A1 | 9/2011 | Simmons | |
| 2011/0229352 A1 | 9/2011 | Herbert | |
| 2011/0236265 A1 | 9/2011 | Hasui et al. | |
| 2011/0236277 A1 | 9/2011 | Lee et al. | |
| 2011/0248653 A1* | 10/2011 | Brotto | B25F 5/021 318/139 |
| 2011/0251569 A1 | 10/2011 | Turner et al. | |
| 2011/0257572 A1 | 10/2011 | Locke et al. | |
| 2011/0311379 A1 | 12/2011 | Hale et al. | |
| 2012/0000208 A1 | 1/2012 | Hon et al. | |
| 2012/0008817 A1 | 1/2012 | Grinker et al. | |
| 2012/0046625 A1 | 2/2012 | Johannison | |
| 2012/0053541 A1 | 3/2012 | Yao et al. | |
| 2012/0078539 A1* | 3/2012 | Vernon-Harcourt | A61M 1/0031 702/50 |
| 2012/0095380 A1 | 4/2012 | Gergeley et al. | |
| 2012/0184930 A1 | 7/2012 | Johannison | |
| 2012/0203177 A1* | 8/2012 | Lanier, Jr. | A61M 5/14224 604/151 |
| 2012/0220960 A1 | 8/2012 | Ruland | |
| 2012/0251359 A1 | 10/2012 | Neelakantan et al. | |
| 2012/0259299 A1 | 10/2012 | Ryu et al. | |
| 2012/0271256 A1 | 10/2012 | Locke et al. | |
| 2012/0289895 A1 | 11/2012 | Tsoukalis | |
| 2012/0289913 A1 | 11/2012 | Eckstein et al. | |
| 2012/0289914 A1 | 11/2012 | Eckstein et al. | |
| 2012/0301341 A1 | 11/2012 | Ota et al. | |
| 2013/0017110 A1 | 1/2013 | Villagomez et al. | |
| 2013/0042753 A1 | 2/2013 | Becker et al. | |
| 2013/0066285 A1 | 3/2013 | Locke et al. | |
| 2013/0066289 A1 | 3/2013 | Song et al. | |
| 2013/0085462 A1 | 4/2013 | Nip et al. | |
| 2013/0090613 A1 | 4/2013 | Kelch et al. | |
| 2013/0090616 A1 | 4/2013 | Neubauer | |
| 2013/0116635 A1 | 5/2013 | Fleischmann | |
| 2013/0118622 A1 | 5/2013 | Patzold et al. | |
| 2013/0123755 A1 | 5/2013 | Locke et al. | |
| 2013/0138054 A1 | 5/2013 | Fleischmann | |
| 2013/0144230 A1 | 6/2013 | Wu et al. | |
| 2013/0150814 A1 | 6/2013 | Buan | |
| 2013/0165878 A1 | 6/2013 | Heagle | |
| 2013/0209277 A1 | 8/2013 | Locke et al. | |
| 2013/0209279 A1 | 8/2013 | Locke et al. | |
| 2013/0209281 A1 | 8/2013 | Locke et al. | |
| 2013/0213506 A1 | 8/2013 | Chen et al. | |
| 2013/0223979 A1 | 8/2013 | Locke et al. | |
| 2013/0267917 A1 | 10/2013 | Pan et al. | |
| 2013/0274688 A1 | 10/2013 | Weston | |
| 2013/0280113 A1 | 10/2013 | Miranda et al. | |
| 2013/0331822 A1 | 12/2013 | Patel et al. | |
| 2013/0340870 A1 | 12/2013 | Ito et al. | |
| 2014/0072149 A1 | 3/2014 | Yan et al. | |
| 2014/0100516 A1 | 4/2014 | Hunt et al. | |
| 2014/0114236 A1 | 4/2014 | Gordon | |
| 2014/0114237 A1 | 4/2014 | Gordon | |
| 2014/0114268 A1 | 4/2014 | Auguste et al. | |
| 2014/0163490 A1 | 6/2014 | Locke et al. | |
| 2014/0194835 A1 | 7/2014 | Ehlert | |
| 2014/0228791 A1 | 8/2014 | Hartwell | |
| 2014/0236106 A1 | 8/2014 | Locke et al. | |
| 2014/0236109 A1 | 8/2014 | Greener | |
| 2014/0249493 A1 | 9/2014 | Hartwell | |
| 2014/0276487 A1 | 9/2014 | Locke et al. | |
| 2014/0303551 A1 | 10/2014 | Germain et al. | |
| 2014/0316359 A1 | 10/2014 | Collinson et al. | |
| 2014/0323906 A1 | 10/2014 | Peatfield et al. | |
| 2015/0025482 A1 | 1/2015 | Begin et al. | |
| 2015/0032035 A1 | 1/2015 | Banwell et al. | |
| 2015/0065965 A1 | 3/2015 | Haggstrom et al. | |
| 2015/0073363 A1 | 3/2015 | Kelch et al. | |
| 2015/0094673 A1 | 4/2015 | Pratt et al. | |
| 2015/0094674 A1 | 4/2015 | Pratt et al. | |
| 2015/0159066 A1 | 6/2015 | Hartwell et al. | |
| 2015/0174304 A1 | 6/2015 | Askem et al. | |
| 2015/0209492 A1 | 7/2015 | Blott et al. | |
| 2015/0308994 A1 | 10/2015 | Hammond et al. | |
| 2015/0320604 A1 | 11/2015 | Adie et al. | |
| 2016/0081859 A1 | 3/2016 | Hartwell | |
| 2016/0144084 A1 | 5/2016 | Collinson et al. | |
| 2016/0298620 A1 | 10/2016 | Cordoba et al. | |
| 2016/0317357 A1 | 11/2016 | Vitaris et al. | |
| 2016/0319957 A1 | 11/2016 | Jaeb et al. | |
| 2017/0095598 A1 | 4/2017 | Joshi et al. | |
| 2017/0128642 A1 | 5/2017 | Buan | |
| 2017/0181896 A1 | 6/2017 | Hartwell | |
| 2017/0181897 A1 | 6/2017 | Hartwell | |

FOREIGN PATENT DOCUMENTS

| | | |
|---|---|---|
| DE | 20 2004 017 052 | 7/2005 |
| EP | 0 208 395 | 1/1987 |
| EP | 0 257 916 | 3/1988 |
| EP | 0 340 018 | 11/1989 |
| EP | 0 759 521 | 2/1997 |
| EP | 0 775 825 | 5/1997 |
| EP | 0 793 019 | 9/1997 |
| EP | 0 809 028 | 11/1997 |
| EP | 0 898 076 | 2/1999 |
| EP | 1 449 971 | 8/2004 |
| EP | 1 476 217 | 11/2004 |
| EP | 2 161 448 | 3/2010 |
| EP | 2 216 573 | 8/2010 |
| EP | 2 302 127 A1 | 3/2011 |
| EP | 2 366 721 | 9/2011 |
| EP | 2 021 046 | 3/2012 |
| EP | 2 462 908 | 6/2012 |
| EP | 2 544 642 | 1/2015 |
| EP | 2 648 668 | 1/2015 |
| FR | 1163907 | 10/1958 |
| GB | 1255395 | 12/1971 |
| GB | 2273133 | 6/1994 |
| GB | 2306580 | 5/1997 |
| GB | 2433298 | 3/2007 |
| JP | 2005-500141 | 1/2005 |
| JP | 2010-506691 | 3/2010 |
| RU | 2428208 | 9/2011 |

(56) References Cited

FOREIGN PATENT DOCUMENTS

| | | |
|---|---|---|
| RU | 2429024 | 9/2011 |
| WO | WO 1983/00742 | 3/1983 |
| WO | WO 1994/21312 | 9/1994 |
| WO | WO 1995/29959 | 11/1995 |
| WO | WO 1996/05873 | 2/1996 |
| WO | WO 98/19068 | 5/1998 |
| WO | WO 1998/19068 | 5/1998 |
| WO | WO 2000/000743 | 1/2000 |
| WO | WO 2000/49968 | 8/2000 |
| WO | WO 2000/56378 | 9/2000 |
| WO | WO 2000/079154 | 12/2000 |
| WO | WO 2003/085810 | 10/2003 |
| WO | WO 2004/007960 | 1/2004 |
| WO | WO 2004/081421 | 9/2004 |
| WO | WO 2005/025447 | 3/2005 |
| WO | WO 2005/123170 | 12/2005 |
| WO | WO 2006/052839 | 5/2006 |
| WO | WO 2006/058801 | 6/2006 |
| WO | WO 2006/062276 | 6/2006 |
| WO | WO 2006/092333 | 9/2006 |
| WO | WO 2006/117207 | 11/2006 |
| WO | WO 2008/031418 | 3/2008 |
| WO | WO 2008/039223 | 4/2008 |
| WO | WO 2008/048481 | 4/2008 |
| WO | WO 2008/049029 | 4/2008 |
| WO | WO 2009/047524 | 4/2009 |
| WO | WO 2009/066105 | 5/2009 |
| WO | WO 2009/095170 | 8/2009 |
| WO | WO 2009/124100 | 10/2009 |
| WO | WO 2009/158128 | 12/2009 |
| WO | WO 2010/142959 | 12/2010 |
| WO | WO 2011/082461 | 7/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/148188 | 12/2011 |
| WO | WO 2012/038724 | 3/2012 |
| WO | WO 2012/048179 | 4/2012 |
| WO | WO 2012/088572 | 7/2012 |
| WO | WO 2012/041296 | 8/2012 |
| WO | WO 2012/131237 | 10/2012 |
| WO | WO 2012/140180 | 10/2012 |
| WO | WO 2012/140378 | 10/2012 |
| WO | WO 2012/143665 | 10/2012 |
| WO | WO 2013/006932 | 1/2013 |
| WO | WO 2013/010907 | 1/2013 |
| WO | WO 2013/019017 | 2/2013 |
| WO | WO 2013/064852 | 5/2013 |
| WO | WO 2013/065423 | 5/2013 |
| WO | WO 2013/083800 | 6/2013 |
| WO | WO 2013/090810 | 6/2013 |
| WO | WO 2013/117945 | 8/2013 |
| WO | WO 2013/118447 | 8/2013 |
| WO | WO 2013/119854 | 8/2013 |
| WO | WO 2013/133652 | 9/2013 |
| WO | WO 2013/140255 | 9/2013 |
| WO | WO 2013/149078 | 10/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/108476 | 7/2014 |
| WO | WO 2014/113253 | 7/2014 |
| WO | WO 2015/022334 | 2/2015 |
| WO | WO 2015/022340 | 2/2015 |
| WO | WO 2015/023515 | 2/2015 |
| WO | WO 2015/031216 | 3/2015 |

OTHER PUBLICATIONS

Japanese Office Action, re JP Application No. 2015-501005, dated Feb. 20, 2017.
Chinese First Office Action and Search Report, re CN Application No. 201380026365.5, dated Jan. 4, 2016.
U.S. Appl. No. 61/828,604, filed May 29, 2013, Collinson et al.
U.S. Appl. No. 61/829,187, filed May 30, 2013, Collinson et al.
U.S. Appl. No. 61/906,865, filed Nov. 20, 2013, Collinson et al.
U.S. Appl. No. 61/907,350, filed Nov. 21, 2013, Collinson et al.
Australian Exam Report, re AU Application No. 2013237095, dated Oct. 14, 2016.
Chinese Second Office Action, re CN Application No. 201380026365.5, dated Sep. 28, 2016.
International Search Report and Written Opinion, re PCT Application No. PCT/EP2015/063373, dated Sep. 2, 2015.
International Search Report for International Application No. PCT/EP2014/071510 dated Feb. 5, 2015 in 7 pages.
International Preliminary Report for Patentability in International Application No. PCT/EP2014/071510 dated Apr. 21, 2016 in 12 pages.
International Search Report for International Application No. PCT/EP2014/071520 dated Feb. 2, 2015 in 5 pages.
International Preliminary Report for Patentability Application No. PCT/EP2014/071520 dated Apr. 21, 2016 in 8 pages.
Mexican Office Action, re MX Application No. MX/a/2014/011314, dated Dec. 5, 2016.
Russian Office Action and Search Report, re RU Application No. 2014138377, FA email dated Feb. 7, 2017.
International Search Report and Written Opinion re PCT/IB2013/000866, dated Jul. 29, 2013.
International Search Report and Written Opinion for PCT Application No. PCT/GB2014/050786, dated Jun. 12, 2014.
Kendall ULTEC Hydrocolloid Dressing (4"x4"), product ordering page, web page downloaded Jul. 13, 2014.
Protz, Kerstin: "Modern Wundauflagen unterstutzen Heilungsprozess", Wundversorgung : Indikation und Anwendung, Geriatrie Journal Apr. 2005, pp. 3333-3339, with translation.
Australian Office Action, re AU Application No. 2013237095, dated May 30, 2017.
International Preliminary Report on Patentability, re PCT Application No. PCT/IB2013/000866, dated Oct. 2, 2014.
Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.
Mexican Office Action, re MX Application No. MX/a/2014/011314, dated May 10, 2017.
Russian Office Action, re RU Application No. 2014138377, dated Apr. 17, 2017.
Smith & Nephew, "PICO Single Use Negative Pressure Wound Therapy System", spiral booklet, Mar. 2011, in 7 pages.

* cited by examiner

CONTROLLING OPERATION OF A REDUCED PRESSURE THERAPY SYSTEM BASED ON DYNAMIC DUTY CYCLE THRESHOLD DETERMINATION

CROSS-REFERENCE TO RELATED APPLICATIONS

This application is a national stage application of International Patent Application No. PCT/IB2013/000866, filed on Mar. 13, 2013, which claims priority to U.S. Provisional Patent Application No. 61/613,456, filed on Mar. 20, 2012, which are incorporated by reference it their entirety and are made part of this disclosure.

BACKGROUND

Field

Embodiments of the present disclosure relate to methods and apparatuses for dressing and treating a wound with topical negative pressure (TNP) therapy. In particular, but without limitation, embodiments disclosed herein relate to negative pressure therapy pumps and dressings, and methods and algorithms for controlling the operation of TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

SUMMARY

Embodiments disclosed herein relate to systems and methods of treating a wound with reduced or negative pressure and are generally applicable to use in topical negative pressure (TNP) therapy systems. Some embodiments are directed to negative pressure therapy pumps and dressings, and methods and algorithms for operating such negative pressure therapy pumps and TNP systems for use with negative pressure therapy dressings. Some embodiments disclosed herein comprise novel and inventive control logic configured to control the operation of a TNP system. For example, some embodiments comprise novel and inventive control logic configured to control the operation of a source of negative pressure in response to monitoring and detecting various operating conditions. In some embodiments, the control logic can be configured to detect and respond to one or more leaks, such as leaks in a dressing that is in fluid communication with a source of negative pressure, leaks in a seal created by a dressing over a wound, and the like.

In some embodiments, apparatuses and methods for controlling the operation of a reduced pressure therapy system based on dynamic duty cycle threshold determination are disclosed. In certain embodiments, an apparatus for applying negative pressure to a wound includes a source of negative pressure configured to be coupled to a dressing, a power source configured to supply power to the source apparatus, and a controller. The controller is configured to monitor a duty cycle of the source of negative pressure and determine a duty cycle threshold based at least in part on a capacity of the power source and operational time of the apparatus. In various embodiments, the duty cycle reflects an amount of time the source of negative pressure is active over a period of time. In certain embodiments, the controller is configured to determine the duty cycle threshold according to a quadratic function. In some embodiments, the capacity of the power source and the operational time are related according to a linear relationship. According to various embodiments, the controller is also configured to measure a first capacity of the power source when the source of negative pressure is active, measure a second capacity of the power source when the source of negative pressure is inactive, and determine the capacity of the power source based at least in part on the first and second capacities of the power source. For example, the capacity of the power source can be determined based on a mean value of the first and second capacities of the power source.

In some embodiments, a method for operating a negative pressure apparatus having a source of negative pressure and a power source includes delivering negative pressure to a dressing positioned over a wound from the source of negative pressure, monitoring a duty cycle of the source of negative pressure, and determining a duty cycle threshold based at least in part on a capacity of the power source and an operational time of the negative pressure apparatus. In various embodiments, the duty cycle reflects an amount of time the source of negative pressure is active over a period of time. In certain embodiments, the determination of the duty cycle threshold is performed according to a quadratic function. In some embodiments, the capacity of the power source and the operational time are related according to a linear relationship. According to certain embodiments, the method also includes measuring a first capacity of the power source when the source of negative pressure is active, measuring a second capacity of the power source when the source of negative pressure is inactive, and determining the capacity of the power source based at least in part on the first and second capacities of the power source. For example, the capacity of the power source can be determined based on a mean value of the first and second capacities of the power source.

BRIEF DESCRIPTION OF THE DRAWINGS

Embodiments of the present invention will now be described hereinafter, by way of example only, with reference to the accompanying drawings in which.

DETAILED DESCRIPTION OF SOME EMBODIMENTS

Overview

Figure 1:
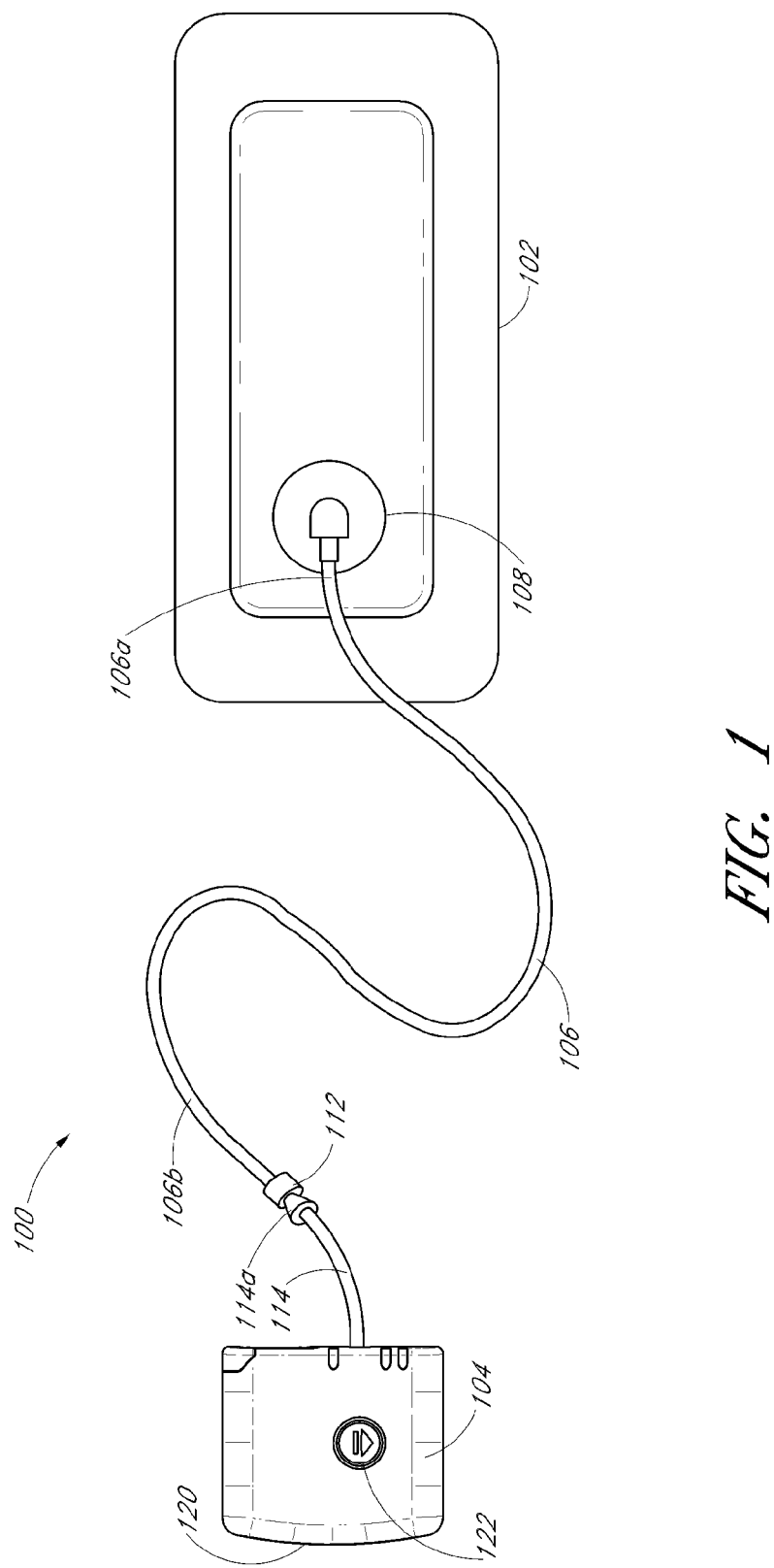
FIG. 1 illustrates an embodiment of a reduced pressure wound therapy apparatus comprising a pump, a dressing, and a conduit.

Embodiments disclosed herein relate to systems and methods of treating a wound with reduced pressure. As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

Embodiments of the present invention are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Some embodiments are directed to negative pressure therapy pumps and dressings, and methods and algorithms for operating such negative pressure therapy pumps and TNP systems for use with negative pressure therapy dressings. Some embodiments of pump assemblies disclosed herein comprise novel and inventive control logic configured to control the operation of a pump assembly. For example, some embodiments comprise novel and inventive control logic configured to control the operation of a pump assembly in response to monitoring and detecting various operating conditions, such as presence and/or severity of a leak or leaks in the system, rate of flow of fluid (e.g., air, liquid and/or solid exudate, etc.) aspirated from a wound, and the like, while prolonging an operational life of the pump assembly and providing optimal or near optimal delivery of therapy to a patient. In some embodiments, the control logic can be configured to detect a leak or leaks in a system (e.g., leak or leaks in the dressing that is in fluid communication with the pump, leak or leaks in the seal created by a dressing over a wound, etc.) as well as to control the operation of the pump assembly when such leak or leaks are detected.

Control logic disclosed herein can help the pump assembly operate more efficiently and conserve power, for example but without limitation, battery power. Some embodiments disclosed herein relate to apparatuses and methods for controlling operation of a negative pressure wound therapy system. In particular, but without limitation, embodiments disclosed herein relate to negative pressure therapy apparatuses and dressings, and methods and algorithms for operating such negative pressure therapy systems. In some embodiments, though not required, an apparatus can comprise a dressing configured to be placed over a wound and to create a substantially fluid impermeable seal over the wound. The apparatus can comprise a source of negative pressure (e.g., a negative pressure pump) configured to be coupled to the dressing. The apparatus can further comprise a controller configured to monitor a duty cycle of the source of negative pressure and determine a duty cycle threshold based at least in part on a capacity of the power source and an operational time of the apparatus. In some embodiments, the controller can be further configured to activate the source of negative pressure, determine if the duty cycle exceeds a duty cycle threshold, and provide an indication in response to the duty cycle exceeding the duty cycle threshold.

Some embodiments disclose a method of operating a source of negative pressure. The method can comprise delivering negative pressure to a dressing positioned over a wound from the source of negative pressure, monitoring a duty cycle of the source of negative pressure, and determining a duty cycle threshold based at least in part on a capacity of the power source and an operational time of the negative pressure apparatus. In some embodiments, the method can further comprise providing an indication in response to determining that the duty cycle exceeds the duty cycle threshold.

In some embodiments, the source of negative pressure can be a miniature, disposable pump, powered by a power source, such as a battery source. The pump assembly can be configured to provide therapy for a predetermined period of time, such as approximately 1 day, 2-10 days, greater than 10 days, etc. In some embodiments, the pump assembly can be required to provide uninterrupted therapy for such period of time. In some embodiments, the pump assembly can be configured to deactivate itself a predetermined period of time (e.g., 7 days, 10 days, etc.) after an initial activation. The algorithms or logic disclosed herein can help the pump assembly operate more efficiently in order to prolong operational life of the pump assembly by, for instance, conserving power (for example, but without limitation, battery power).

In some embodiments, the pump assembly can be configured to monitor the duty cycle of the source of negative pressure (e.g., a pump). As is used herein, "duty cycle" reflects the amount of time the source of negative pressure is active or running over a period of time. In other words, the duty cycle reflects time that the source of negative pressure is in an active state as a fraction of total time under consideration. This can be represented mathematically in one embodiment as:

$$DC = t/T, \qquad (1)$$

where DC is the duty cycle, t is the duration that the source of negative pressure is active, and T is the total time under consideration. Duty cycle can be measured as an absolute value (e.g., X seconds), a proportion (e.g., 1/X), a percentage (e.g., X %), etc. For example, if over a period of 1 minute the source of negative pressure has been on (or operating) for 6 seconds and off (or not operating) for 54 seconds, the duty cycle can be represented as 6 seconds, 1/10, 10%, etc.

In some embodiments, the pump assembly can include a controller configured to monitor the duty cycle of the source of negative pressure. Duty cycle measurements can indicate rate of flow through the system and reflect a level of activity of the source of negative pressure. For example, duty cycle can indicate that the source of negative pressure is operating normally, working hard, working extremely hard, etc. Moreover, duty cycle measurements, such as periodic duty cycle measurements, can reflect various operating conditions, such as presence, rate, and/or severity of one or more leaks in the system, rate of flow of fluid (e.g., air, liquid and/or solid exudate, etc.) aspirated from a wound, and the like. Based on the duty cycle measurements, such as by comparing the measured duty cycle to a duty cycle threshold (determined in calibration or at runtime), the controller can execute and/or be programmed to execute algorithms or logic that control the operation of the system in accordance with various system requirements. For example, duty cycle measurements can indicate presence of a high leak in the system, and the controller can be programmed to indicate this condition to a user (e.g., patient, caregiver, physician, etc.) and/or temporarily suspend or pause operation of the source of negative pressure in order to conserve power.

In some embodiments, the system can be configured to provide indication, alarms, etc. reflecting operating conditions to a user. The system can include visual, audible, tactile, and other types of indicators and/or alarms configured to signal to the user various operating conditions. Such conditions include system on/off, standby, pause, normal operation, dressing problem, leak, error, and the like. The indicators and/or alarms can include speakers, displays, light sources, etc., and/or combinations thereof. For example, indication can be provided by activating or deactivating the source of negative pressure, reducing negative pressure level generated by the source of negative, lowering the amount of power used by the source of negative pressure, etc. or any combination thereof.

Reduced Pressure System

FIG. 1 illustrates an embodiment of a reduced pressure wound treatment apparatus 100 comprising a wound dressing 102 in combination with a pump assembly 104. In any of the apparatus embodiments disclosed herein, as in the embodiment illustrated in FIG. 1, the pump assembly can be a canisterless pump assembly (meaning that the pump assembly does not have an exudate or liquid collection canister). However, any of the pump assembly embodiments disclosed herein can be configured to include or support a canister. Additionally, in any of the apparatus embodiments disclosed herein, any of the pump assembly embodiments can be mounted to or supported by the dressing, or adjacent to the dressing. The dressing 102 may be placed over a wound (not illustrated) as described in greater detail in U.S. Patent Publication No. 2011/0282309 (Exhibit C of U.S. Patent Application No. 61/613,456), the disclosure of which is hereby incorporated by reference and is made part of this disclosure, and a conduit 106 may then be connected to the dressing 102. Dressing 102 or any other dressing disclosed herein can have any of the materials, sizes, components, or other details of any of the dressing embodiments disclosed in U.S. Patent Publication No. 2011/0282309 (Exhibit C of U.S. Patent Application No. 61/613,456), and such embodiments and illustrations thereof are hereby incorporated by reference in their entireties as if made part of this disclosure. The conduit 106 or any other conduit disclosed herein can be formed from polyurethane, PVC, nylon, polyethylene, silicone, or any other suitable material.

Some embodiments of the dressing 102 can have a port 108 configured to receive an end of the conduit 106 (e.g., the first end 106a of the conduit 106), though such port 108 is not required. In some embodiments, the conduit can otherwise pass through and/or under the dressing 108 to supply a source of reduced pressure to a space between the dressing 102 and the wound so as to maintain a desired level of reduced pressure in such space. Some embodiments of the apparatus 100 can be configured such that the first end 106a of the conduit 106 is preattached to the port 108. The conduit 106 can be any suitable article configured to provide at least a substantially sealed fluid flow pathway between the pump assembly 104 and the dressing 102, so as to supply the reduced pressure provided by the pump assembly 104 to the dressing 102.

The dressing 102 can be provided as a single article with all wound dressing elements (including the port 108) preattached and integrated into a single unit. The wound dressing 102 may then be connected, via the conduit 106, to a source of negative pressure such as the pump assembly 104. In some embodiments, though not required, the pump assembly 104 can be miniaturized and portable like the PICO pump available from Smith & Nephew, although larger conventional pumps such as the RENASYS GO or RENASYS EZ pumps available from Smith & Nephew can also be used with the dressing 102.

The wound dressing 102 can be located over a wound site to be treated. The dressing 102 can form a substantially sealed cavity or enclosure over the wound site. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

Some embodiments of the apparatus are designed to operate without the use of an exudate canister. The dressing 102 can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. The pump can be programmed to automatically terminate therapy after a desired number of days, e.g., after seven days, further operation of the pump will not be possible. Some embodiments are designed for longer or repeated usage, and can be configured to support an exudate canister.

In some embodiments, the tubing 106 can have a connector 112 positioned at a second end 106b of the tubing 106. The connector 112 can be configured to couple with a short length of conduit 114 projecting from the pump assembly 104, with a mating connector 114a in communication with the short length of conduit 114, with a connector supported by the pump housing (as described in greater detail below), or otherwise. The length of the tubing 114 in some embodiments can be approximately 14 mm (0.55 in), or from approximately 0.5 in to approximately 5 inches. The short length of conduit or tubing 114 can decrease the discomfort to a patient while laying or otherwise resting on the pump and connector 112. Configuring the pump assembly 104 and tubing 106 so that the tubing 106 can be quickly and easily removed from the pump assembly 104 can facilitate or improve the process of dressing or pump changes, if necessary. Any of the pump embodiments disclosed herein can be configured to have any of the connection configurations disclosed herein between the tubing and the pump.

In some embodiments, as in the illustrated embodiment, the pump assembly 104 can be of a sufficiently small and portable size to be supported on a user's body or in a user's clothing. For example, the pump assembly 104 can be sized to be attached using adhesive medical tape or otherwise to a person's skin in a comfortable location, adjacent to or on the dressing 102 or otherwise. Further, the pump assembly 104 can be sized to fit within a person's pants or shirt pocket, or can be tethered to a person's body using a lanyard, pouch, or other suitable device or article.

In some embodiments, the pump assembly 104 can be powered by one or more batteries (for example, two batteries). The negative pressure range for some embodiments of the present disclosure can be approximately −80 mmHg, or between about −20 mmHg and −200 mmHg. Note that these pressures are relative to normal ambient atmospheric pressure thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even 150 mmHg, can be supplied by the apparatus 100. Other details regarding the operation of the pump assembly 104 are set forth in U.S. Patent Publication No. 2011/0282309 (Exhibit C of U.S. Patent Application No. 61/613,456), and such embodiments, configurations, details, and illustrations thereof are hereby incorporated by reference in their entireties as if made part of this disclosure.

The pump assembly 104 can have a housing 120 comprising a control button 122 (which can also be a switch or other similar component) and one or more lights, which can be LED lights. In some embodiments, the pump assembly 104 can have more than one button 122, and can have three or more lights. The lights can be configured to alert a user to a variety of operating and/or failure conditions of the pump assembly 104, including alerting the user to normal or proper operating conditions, pump failure, power supplied to the pump or power failure, the condition or voltage level of the batteries, detection of a leak within the dressing or flow pathway, suction blockage, or any other similar or suitable conditions or combinations thereof.

In operation, the wound dressing 102 is sealed over a wound site forming a wound cavity. The pump assembly 104 provides a source of a negative pressure to the dressing 102. Fluid is drawn towards the orifice through the wound dressing from a wound site below a wound contact layer of the wound dressing 102. The fluid moves towards the orifice through a transmission layer, which could be a layer of porous material located above the contact layer. As the fluid is drawn through the transmission layer, wound exudate is absorbed into the absorbent layer.

Figure 2:
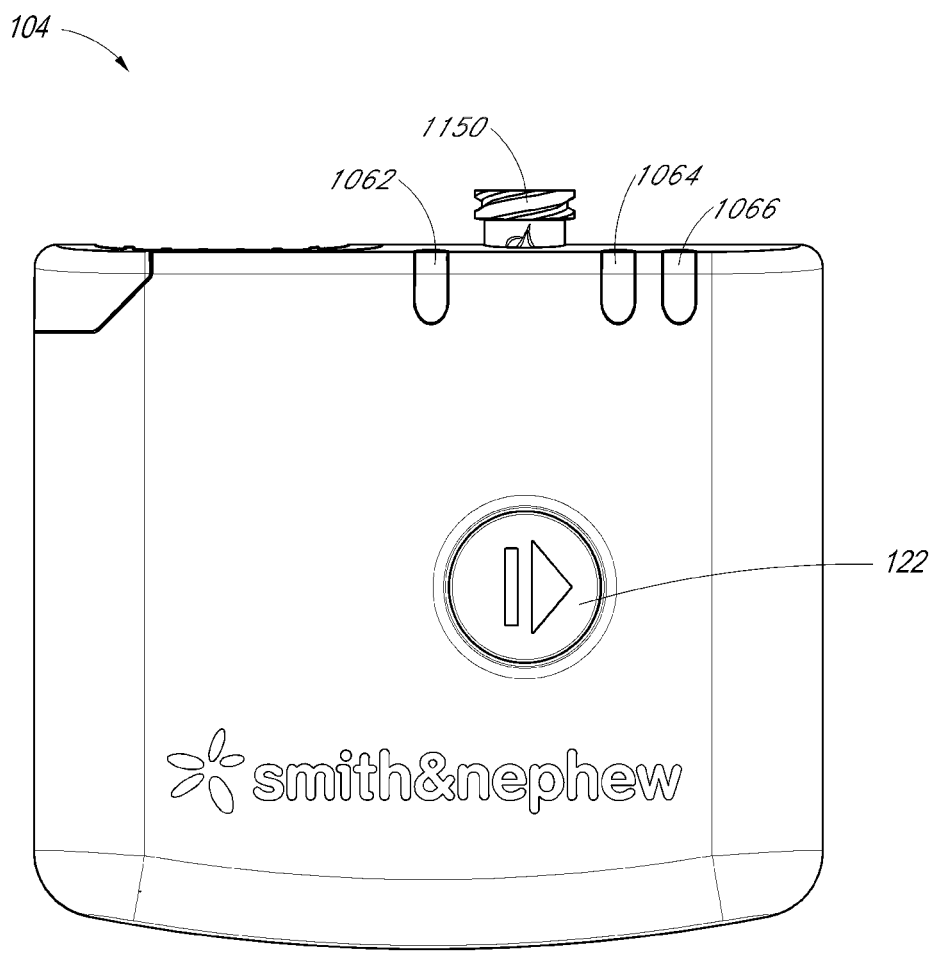
FIG. 2 illustrates a pump assembly according to some embodiments.

FIG. 2 illustrates a pump assembly 104 according to some embodiments. Preferably, the pump assembly 104 can be miniaturized and portable, although larger conventional portable or non-portable (e.g., wall suction) pumps can also be used. The pump assembly 104 can include a switch or a button 122, illustrated as a play/pause button located on the exterior of the housing of the pump assembly. As is disclosed in U.S. patent application Ser. No. 13/287,959 (Exhibit A of U.S. Patent Application No. 61/613,456), published as U.S. Patent Publication No. 2012/0136325, the button 122 can be configured to stop, pause, and/or restart therapy, and such embodiments and illustrations thereof are hereby incorporated by reference in their entireties as if made part of this disclosure. Although illustrated as a press button 122, other types of switches or buttons can be included, such as a touchpad, touch screen, keyboard, and so on.

The pump assembly 104 can further include a connector 1050 (for connecting a conduit, e.g., conduit 106), and three LED indicators 1062, 1064, and 1066. As is illustrated, LED indicator 1062 (e.g., OK indicator) can be configured to indicate normal/abnormal operation of the system. For example, an active (e.g., lit) indicator 1062 can represent normal operation. LED indicator 1064 (e.g., dressing indicator) can be configured to indicate a leak in the system. For example, an active (e.g., lit) indicator 1064 can represent a leak. LED indicator 1066 (e.g., battery indicator) can be configured to indicate a remaining capacity or life of a power source (e.g., batteries). For example, an active (e.g., lit) indicator 1066 can represent a low capacity. In some embodiments, the indicators 1062, 1064, and 1066 can be of a different color, two different colors (e.g., two indicators can share the same color), or same color. Although the pump assembly preferably includes three LED indicators and a push play/pause button, other configurations, locations, and types of indicators, alarms, and switches can alternatively be used. In some embodiments, the pump assembly 104 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources; etc., and/or combinations thereof.

Figure 3:
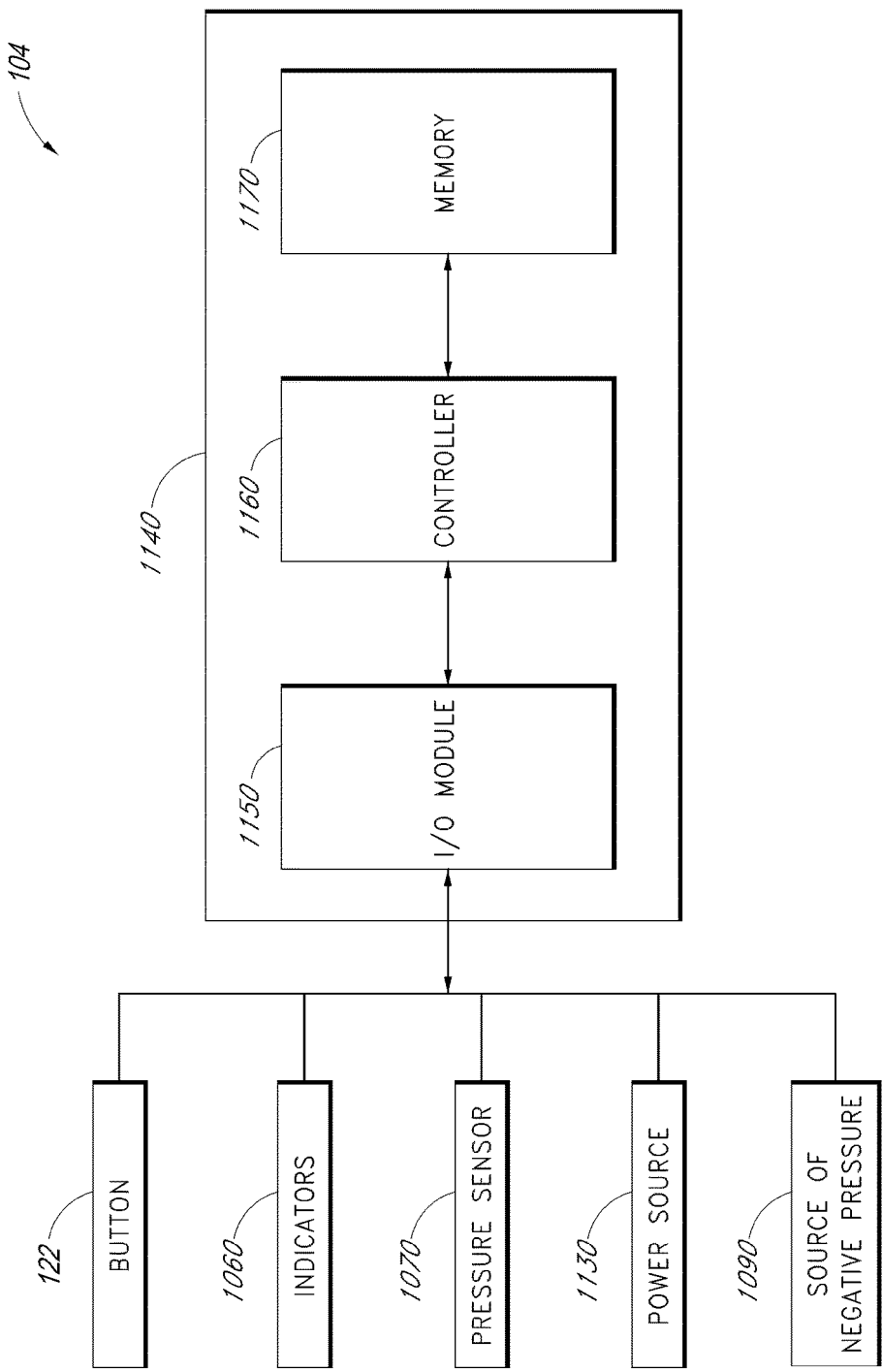
FIG. 3 illustrates an electrical component schematic of a pump assembly according to some embodiments.

FIG. 3 illustrates an electrical component schematic of the pump assembly 104 according to some embodiments. Module 1140, which can be a control board (e.g., printed circuit board assembly), can include an input/output (I/O) module 1150, controller 1160, and memory 1170. In some embodiments, module 1140 can include additional electric/electronic components, for example, fuse or fuses. The controller 1160 can be a microcontroller, processor, microprocessor, etc. or any combination thereof. For example, the controller 1160 can be of STM8L MCU family type from ST Microelectronics, such as STM8L 151G4U6, or of MC9S08QE4/8 series type from Freescale, such as MC9S08QE4CWJ. Preferably, the controller 1160 is a low power or ultra low power device, but other types of devices can alternatively be used. Memory 1170 can include one or more of volatile and/or nonvolatile memory modules, such as one or more of read-only memory (ROM), write once read many memory (WORM), random access memory (e.g., SRAM, DRAM. SDRAM, DDR, etc.), solid-state memory, flash memory, magnetic storage, etc. or any combination thereof. Memory 1170 can be configured to store program code or instructions (executed by the controller), system parameters, operational data, user data, etc. or any combination thereof. In some embodiments, the pump assembly 104 includes multiple controllers.

The I/O module 1150 can be configured to function as an interface between the controller 1160 and other system components that provide and/or are responsive to electromagnetic signals. In other words, the I/O module 1150 can be configured to allow the controller 1160 to monitor the operation of the system and to control other components of the system. In some embodiments, as is illustrated, the I/O module 1150 can be in electromagnetic communication with a button 122, indicators 1060, pressure sensor 1070, power source 1130, and source of negative pressure 1090. The source of negative pressure can be can be of any suitable type such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a voice coil pump, or any other suitable pump or micropump or any combinations of the foregoing. The I/O module can comprise an interface or multiple interfaces configured to communicate with various components. The interface can include standard and/or non-standard ports, such as serial ports, parallel ports, bus interfaces, etc. or any combination thereof.

In some embodiments, the pump assembly 104 can be configured to control the operation of system. For example, the pump assembly 104 can be configured to provide a suitable balance between an uninterrupted delivery of therapy and/or avoidance of inconveniencing the user by, for example, frequently or needlessly pausing or suspending therapy, etc. and conserving power, limiting noise and vibration generated by the negative pressure source, etc. Controlling of the operation of the pump assembly 104 can be performed according to any of the embodiments disclosed in U.S. patent application Ser. No. 13/287,959 (Exhibit A of U.S. Patent Application No. 61/613,456), published as U.S. Patent Publication No. 2012/0136325, and/or International Application No. PCT/GB2011/051745 (Exhibit B of U.S. Patent Application No. 61/613,456), published as WO 2012/038724, and such embodiments and illustrations thereof are hereby incorporated by reference in their entireties as if made part of this disclosure. Various methods or algorithms of controlling the operation of the pump assembly 104 can be executed by the controller 1160, which can be configured to activate/deactivate the source of negative pressure 1090, provide indications to the user, and respond to signals provided by the button 122, etc.

In some embodiments, the pump assembly 104 can be configured to monitor a duty cycle of the source of negative pressure 1090. For example, the controller 1160 can be configured to monitor the duty cycle periodically and/or continuously. Duty cycle measurements can reflect various operating conditions of the system, such as presence and/or severity of leaks, rate of flow of fluid (e.g., air, liquid and/or solid exudate, etc.) aspirated from wound, and so on. For example, duty cycle measurements can indicate presence of a high leak, and the pump assembly can be configured to indicate this condition and/or temporarily suspend or pause operation of the pump in order to conserve power. This functionality can, for example, conserve battery power and allow transient and/or non-transient leaks to become resolved without user intervention or allow the user to fix the leak (e.g., straighten the dressing, fix the seal, check the connection or connections, etc.).

In some embodiments, the pump assembly 104 can be configured to periodically monitor the duty cycle, such as once between every 10 seconds or less and 5 minutes or more. In some embodiments, the pump assembly can be configured to monitor the duty cycle once per minute. As is explained above, duty cycle can be represented mathematically as:

$$DC = t/T \quad (2)$$

where DC is the duty cycle, t is the duration that the source of negative pressure is active, and T is the total time under consideration. In case of monitoring the duty cycle once per minute (i.e., T=60 seconds), the duty cycle can be expressed (e.g., in percent) as:

$$DC = (\text{Pump run time during the elapsed minute}/60)*100\% \quad (3)$$

Figure 4:
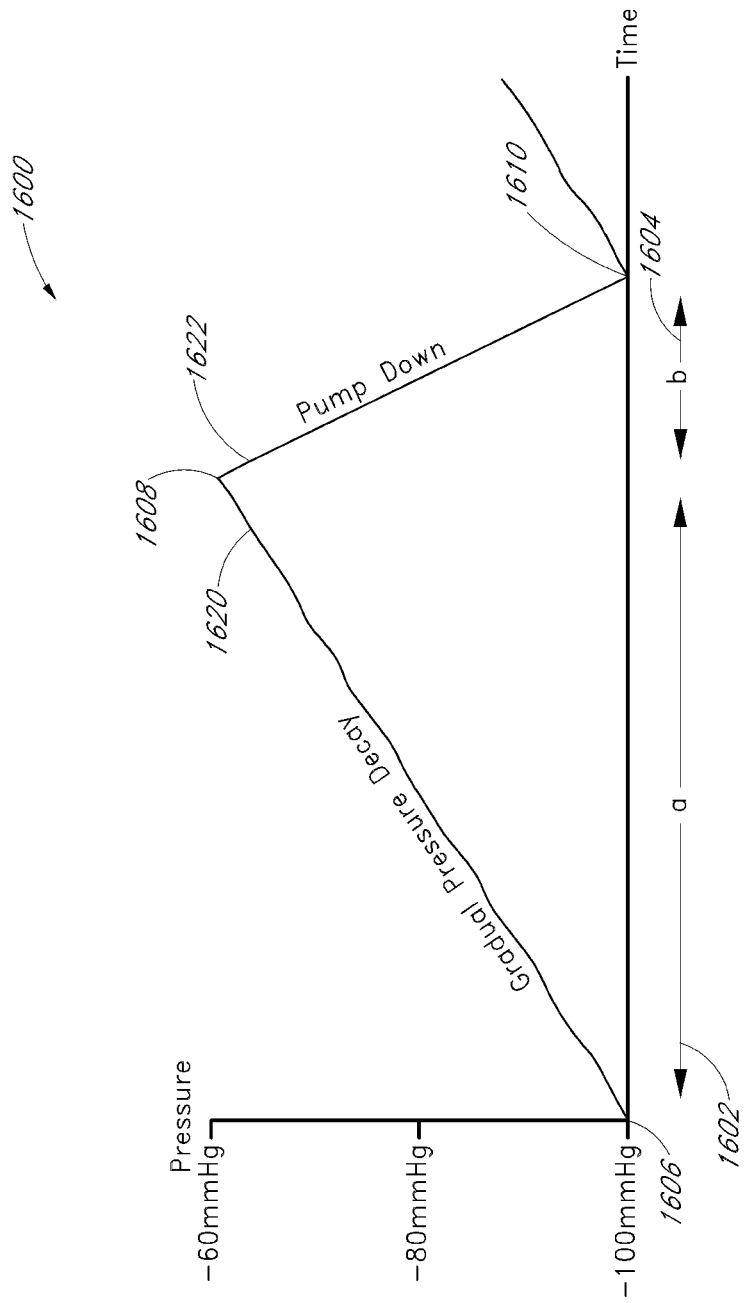
FIG. 4 illustrates a graph depicting a duty cycle determination for a pump assembly according to some embodiments.

FIG. 4 illustrates a graph 1600 depicting a duty cycle determination for the pump assembly 104 according to some embodiments. The x-axis represents time and the y-axis represents pressure. In some embodiments, the pump assembly 104 can be configured to establish a desired negative pressure level of −100 mmHg under the dressing 102, as is represented by position 1606. For example, this can be performed during an initial pump down in state 1260, as is disclosed in U.S. patent application Ser. No. 13/287,959 (Exhibit A of U.S. Patent Application No. 61/613,456), published as U.S. Patent Publication No. 2012/0136325, and such embodiments and illustrations thereof are hereby incorporated by reference in their entireties as if made part of this disclosure. The pump assembly can be configured to monitor the level of negative pressure under the dressing 102. For example, this can be performed in the monitor state 1280, as is disclosed in U.S. patent application Ser. No. 13/287,959 (Exhibit A of U.S. Patent Application No. 61/613,456), published as U.S. Patent Publication No. 2012/0136325, and such embodiments and illustrations thereof are hereby incorporated by reference in their entireties as if made part of this disclosure. As is illustrated, the pump assembly can monitor pressure over the period of time a, as represented by interval 1602. The level of negative pressure under the dressing 102 can decay over time (e.g., due to leaks in the system), as is illustrated by line 1620.

In some embodiments, the pump assembly 104 can be configured to restore or reestablish the negative pressure level under the dressing 102 when that pressure decays to reach or pass a threshold of approximately −60 mmHg, as is represented by position 1608. In some embodiments, the pump assembly can be configured to activate the pump, as is illustrated by line 1622. For example, this can be performed by transitioning to the maintenance pump down state 1290, as is disclosed in U.S. patent application Ser. No. 13/287,959 (Exhibit A of U.S. Patent Application No. 61/613,456), published as U.S. Patent Publication No. 2012/0136325, and such embodiments and illustrations thereof are hereby incorporated by reference in their entireties as if made part of this disclosure. As is illustrated, the pump assembly can activate the pump for a time duration b (1604) until the negative pressure level of −100 mmHg is reestablished under the dressing 102. The pump assembly can be configured to deactivate the pump when the level of pressure under the dressing 102 reaches −100 mmHg at position 1610. For example, this can be performed by transition to the monitor state 1280, as is disclosed in U.S. patent application Ser. No. 13/287,959 (Exhibit A of U.S. Patent Application No. 61/613,456), published as U.S. Patent Publication No. 2012/0136325, and such embodiments and illustrations thereof are hereby incorporated by reference in their entireties as if made part of this disclosure. The duty cycle (DC) over the period illustrated in 1600 (i.e., a+b) can be expressed (e.g., in percent) as:

$$DC=100\%*[b/(a+b)] \quad (4)$$

In order to determine the duty cycle, the pump assembly 104 can be configured to monitor the duration of time that the pump has been active (e.g., the pump run time) and/or inactive. In some embodiments, the pump assembly (e.g., controller 1160) can be configured to compare the determined duty cycle to a duty cycle threshold, which can be selected from the range between 1% or less and 50% or more (e.g., 9%). The comparison can, for example, indicate presence of a leak in the system. In other words, if the pump remains active over a period of time so that the duty cycle threshold is reached or exceeded, the source of negative pressure may be working too hard to overcome the leak. In such cases, the pump assembly can be configured to suspend or pause the delivery of therapy. The pump assembly can be configured to provide an indication to the user that the pump is working hard (e.g., duty cycle exceeds the duty cycle threshold) by, for example, deactivating the source of negative pressure. In some embodiments, the duty cycle threshold can be a preset value, set or changed by the user, and/or varied based on various operating conditions or on any combination thereof.

Dynamic Duty Cycle Threshold Determination

In some embodiments, the pump assembly 104 determines and adjusts the duty cycle threshold at run time (or dynamically). For example, the controller 1160 can be configured to determine the duty cycle threshold periodically and/or continuously, such as approximately every 1 second or less, 30 seconds or less or more, 1 minute or less or more, 10 minutes or less or more, 30 minutes or less or more, 1 hour or less or more, and so on. The duty cycle threshold can be based at least in part on a capacity of the power source 1130 and an operational time of the apparatus (e.g., pump assembly 104). As explained above, the pump assembly can be configured to provide therapy for a predetermined period of time, and deactivate itself a predetermined period of time after an initial activation. For instance, such predetermined period of time (or lifetime threshold) can be between 1 day or less or 10 days or more, such as 7 days (or 168 hours), 10 days (or 240 hours), etc. The power source 1130 can be configured or selected to have sufficient capacity to provide power to the pump assembly 104 until the pump assembly has been in operation for an amount of time that equals or exceeds the lifetime threshold. In some embodiments, the apparatus (e.g., via controller 1160) can be configured to determine the operational time based on a total elapsed time since an initial activation of the apparatus and disable activation of the source of negative pressure when the operational time reaches the lifetime threshold.

In certain embodiments, the determined duty cycle is communicated to the user using the indicators 1060. Because the duty cycle can be correlated with the leak rate experienced the by the system, it can be advantageous for the user to know the leak rate. The duty cycle can be indicated using the LEDs 1062, 1064, and 1066, which can be flashed and/or lit in any suitable sequence when the determined duty cycle falls into a particular range. For example, when the determined duty cycle is between 0% and 2%, LEDs 1062 and 1064 can be turned off and LED 1066 can be turned on or can be flashing. As another example, the duty cycle can be indicated via a beep sequence played back by a speaker or the duty cycle can be displayed on a screen. In some embodiments, the pump assembly 104 is configured to indicate the measured duty cycle by pressing the button 122 for a suitable period of time, such as for 3 seconds. Multiple determined duty cycle values can be combined, such as averaged, and the combined duty cycle value can be indicated to the user. In various embodiments, other operating parameters are indicated to the user. Such operating parameters include power source capacity, total operational time, leak rate (as measured directly or indirectly), and the like.

According to some aspects, adjusting the duty cycle threshold may be beneficial for several reasons. In some embodiments, the duty cycle threshold can represent a balance between the desire to provide therapy to the user with none or fewer interruptions and the need to conserve power. For example, in a situation when there is a leak in the system, the pump assembly 104 can be configured to provide therapy for a certain period of time before providing an indication to the user that a leak has been detected, which can include deactivating the delivery of therapy. After the leak has been remedied, delivery of therapy can be restarted. However, increasing the duty cycle threshold can advantageously result in fewer interruptions of the delivery of therapy.

In some embodiments, the duty cycle threshold can be determined based at least on the capacity of the power source 1130 and the operational time of the pump assembly 104. The controller 1160 can be configured to monitor the operational time (or remaining lifetime) of the pump assembly and the capacity of power source. The controller 1160 can be configured to monitor the operational time of the pump assembly 104 by, for example, maintaining and periodically updating a counter. The capacity of the power source can be monitored, for example, by measuring the voltage of the power source, current of the power source, etc. A dedicated circuit (e.g., a resistor placed in series or parallel with the power source), sensor, or combination thereof can be employed to monitor the capacity of the power source.

In some embodiments, the duty cycle threshold can be represented as a function of two variables as follows:

$$DC\ threshold=C_1\times(\text{operational time}+C_2)\times(\text{capacity}+C_3) \quad (5)$$

where $C_1$, $C_2$, and $C_3$ are constants and capacity is the capacity of the power source.

Figure 5A:
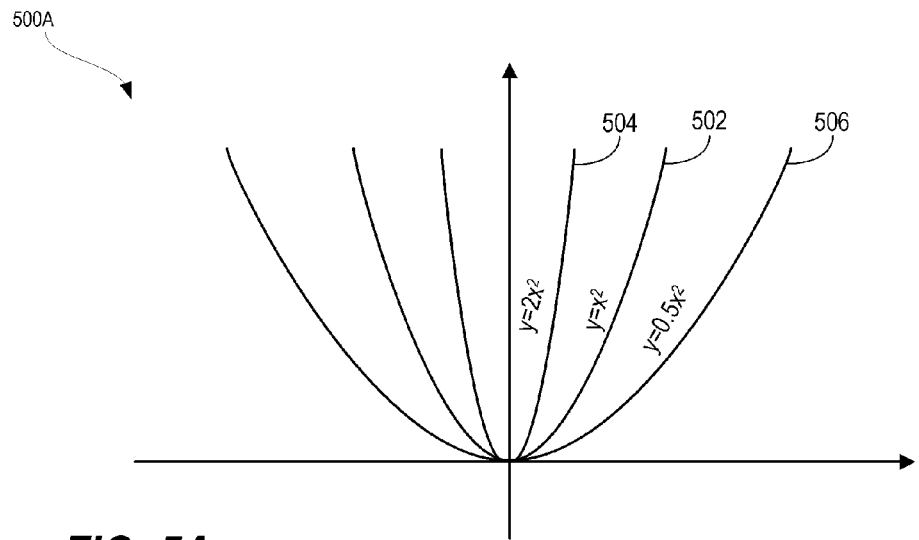
FIGS. 5A-5C illustrate graphs that can be used for determining a duty cycle threshold according to some embodiments.
Figure 5B:
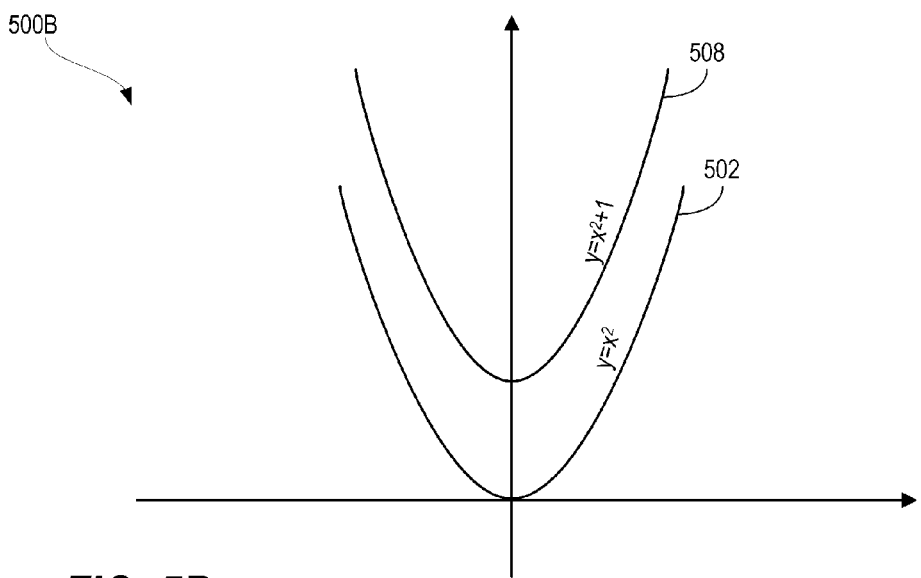
Figure 5C:
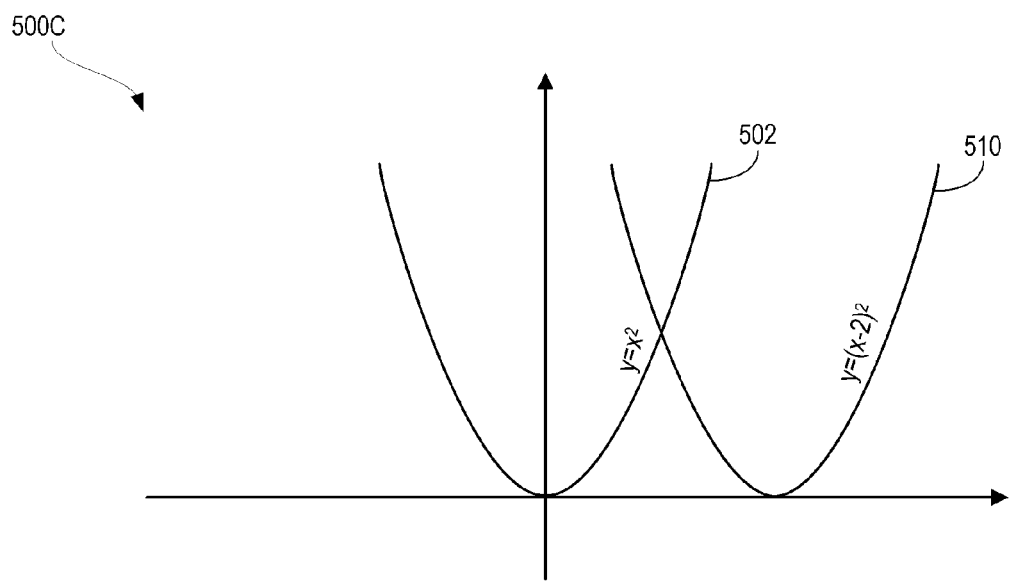

Because the operational time and capacity of power source are related, function (5) can be represented as a quadratic function according to some embodiments. As is depicted by graphs 500A, 500B, and 500C in FIGS. 5A, 5B, and 5C respectively, a duty cycle determination or adjustment tailored to a particular set of system requirements can be obtained by varying the constants of a quadratic equation as follows:

$$f(x)=a*x^2+b*x+c \quad (6)$$

where a, b, and c are constants and x is a variable that corresponds to the capacity of the power source and operational time. Equation 6 can be rewritten as:

$$f(x)=\alpha*(x-\beta)^2+\gamma \quad (7)$$

where $\alpha$, $\beta$, and $\gamma$ are constants. Value of $\alpha$ affects the rate of increase or gradient of the graph, while values of $\beta$ and $\gamma$ are cause the graph to move horizontally and vertically. As is illustrated in FIG. 5A, selecting $\alpha$ that is greater than one (e.g., α>1) provides a more rapidly increasing function, such as $f(x)=2x^2$, (e.g., represented by a narrower graph 504) than a reference function, such as $f(x)=x^2$, (e.g., represented graph 502). Similarly, selecting α that is smaller than one but is positive (e.g., 0<α<1) provides a less rapidly increasing function, such as $f(x)=0.5x^2$, (e.g., represented by a wider graph 506) than the reference function (e.g., represented by graph 502). As is depicted in FIG. 5B, selecting a positive γ (e.g., γ>0), such as $f(x)=x^2+1$, results in moving the graph upward (e.g., graph 508) as compared with the reference function (e.g., represented by graph 502). Similarly, selecting a negative γ (e.g., γ<0) results in moving the graph downward (not shown) as compared with the reference function. As is illustrated in FIG. 5C, selecting a positive β (e.g., β>0), such as $f(x)=(x-2)^2$, results in moving the graph to the right (e.g., graph 510) as compared with the reference function (e.g., represented by graph 502). Similarly, selecting a negative β (e.g., β<0), results in moving the graph to the left (not shown) as compared with the reference function.

Accordingly, in some embodiments, the constants α, β, and γ in equation (7) can be selected and/or adjusted at runtime so as to tailor the duty cycle threshold determination in accordance with a particular set of requirements. For example, as the pump assembly 104 approaches the end of life (e.g., operational time approaches the lifetime threshold, such as 7 days, 10 days, etc.), it can be advantageous to increase the duty cycle threshold when the capacity of the power source is still relatively sufficient. Increasing the duty cycle threshold causes an increase in the allowed duty cycle of the source of negative pressure 1090. In turn, this allows the source of negative pressure to remain active over a longer period of time. As a result, therapy is provided for a longer period of time even if leaks are present in the system. As another example, because the duty cycle threshold is a positive value, a modulus function (e.g., $|f(x)|$ or $abs(f(x))$) may be applied the duty cycle threshold determined according to any equation disclosed herein to ensure that the resulting duty cycle threshold is positive.

In some embodiments, the constants α, β, and γ can be preselected or predetermined values. In some embodiments, the constants α, β, and γ can be adjusted at runtime (or over the operational life of the pump assembly 104). Such adjustment can be performed in response to a change in or detection of various operational conditions, such as frequency of detection of leaks, severity of leaks, type of therapy being delivered (e.g., continuous, intermittent, etc.), duration of various types of therapy, frequency of delivery of various types of therapy, and so on. The adjustment can be performed periodically, such as every hour or less, every day or less or more, etc.

In some embodiments, the duty cycle threshold can be determined according to a quadratic function. In some embodiments, the duty cycle threshold can be determined according to any other suitable function, such as a linear function and/or equation, a non-linear function and/or equation, and the like. The controller 1160 can be configured to determine the duty cycle threshold, for example, periodically (e.g., every hour). In some embodiments, the controller is configured to determine the duty cycle threshold (DCT) according to the equation:

$$DCT = \alpha \times (\text{capacity of the powersource} - \beta) \times (\text{operational time} - \beta) + \gamma \quad (8)$$

where α, β, and γ are constants. In some embodiments, suitable values of constants are $\alpha = 1/16384$, $\beta = 1460$, and $\gamma = -150$. It will be appreciated that it may be advantageous to set α to a value that is a power of two (e.g., $1/16384$ is $2^{-14}$) in order to reduce the computational complexity of the duty cycle threshold determination. When α is set to a power of two, the controller 1160 can perform bit shift operation(s) instead of performing more computationally intensive multiplication or division operation(s). In some embodiments, the capacity of the power source in equation (8) is represented in hundredth of volts and the operational time is represented in hours. In other embodiments, other representations of the capacity of the power source and/or operational time can be used. In some embodiments, different constants can be subtracted from the capacity of the power source and operational time (e.g., $\beta_1$ and $\beta_2$, which are different). In embodiments where equation (8) is used and $\alpha=1/16384$, $\beta=1460$, and $\gamma=-150$, a modulus function may be applied to the determined duty cycle threshold to ensure that the resulting duty cycle threshold value is positive.

In some embodiments, the determined duty cycle threshold may be bound by a lower bound and/or an upper bound. For example, the duty cycle threshold determined using equation (8) can have a lower bound of approximately 9% or lower and an upper bound of approximately 18% or higher when the source of negative pressure is a Koge Electronics KPV8A-3A pump, as is disclosed in U.S. patent application Ser. No. 13/287,959 (Exhibit A of U.S. Patent Application No. 61/613,456), published as U.S. Patent Publication No. 2012/0136325, and such embodiments and illustrations thereof are hereby incorporated by reference in their entireties as if made part of this disclosure. Other lower and/or upper bound values can be used depending on the characteristics of the source of negative pressure 1090 (e.g., pump efficiency, which can be measured by fluid flow rate). For example, for a more efficient pump, suitable lower and upper bounds can be selected as 10% to 20%, 10% to 25%, 15% to 25%, 15% to 25%, 15% to 30%, 15% to 35%, 20% to 40%, 25% to 30%, 25% to 35%, 25% to 40%, 25% to 45%, 25% to 60%, 30% to 45%, 30% to 50%, 30% to 70%, 35% to 40%, 35% to 45%, 35% to 50%, 35% to 65%, 35% to 70%, 40% to 50%, 40% to 85%, etc. Lower and/or upper bound values can be integer and/or non-integer values.

In some embodiments, the parameters of the duty cycle threshold determination (e.g., constants α, β, and γ) can be preselected and/or adjusted so that the determination of the duty cycle threshold provides a threshold value that is approximately equal to the lower bound (e.g., 9%) when the pump assembly 104 is near the beginning of its operational life. For instance, the duty cycle threshold can be 9% during the first several days of operation of the pump assembly when the lifetime threshold of the pump assembly is 7 days or 10 days (e.g., in presence of a low flow leak, the duty cycle threshold can start at the lower bound and increase after completing approximately the first day of operation). As the pump assembly nears the lifetime threshold (e.g., 7 days, 10 days, etc.), the duty cycle threshold can be increased provided that there is sufficient capacity of the power source (e.g., in presence of a high flow leak, the duty cycle threshold may reach the upper bound near the end of life, such as approximately at the sixth day of operation). For example, if there is sufficient capacity of the power source at day 6 of operation, duty cycle threshold determination can provide a threshold value that is approximately equal to the upper bound (e.g., 18%). In some embodiments, the parameters of the duty cycle threshold determination (e.g., constants α, β, and γ) can be preselected so that the duty cycle threshold is increased near the end of life of the pump assembly 104. In some embodiments, the parameters of the duty cycle threshold determination are adjusted at runtime.

In some embodiments, a suitable range of values of constant α can be selected based at least in part on the desired lower and upper bounds of the duty cycle threshold. As is illustrated in FIGS. 5A-5C, value of α affects the rate of increase or gradient of the quadratic equations (7) and/or (8). Accordingly, value of α is at least partially correlated with the lower and upper bounds of the duty cycle threshold.

Figure 6A:
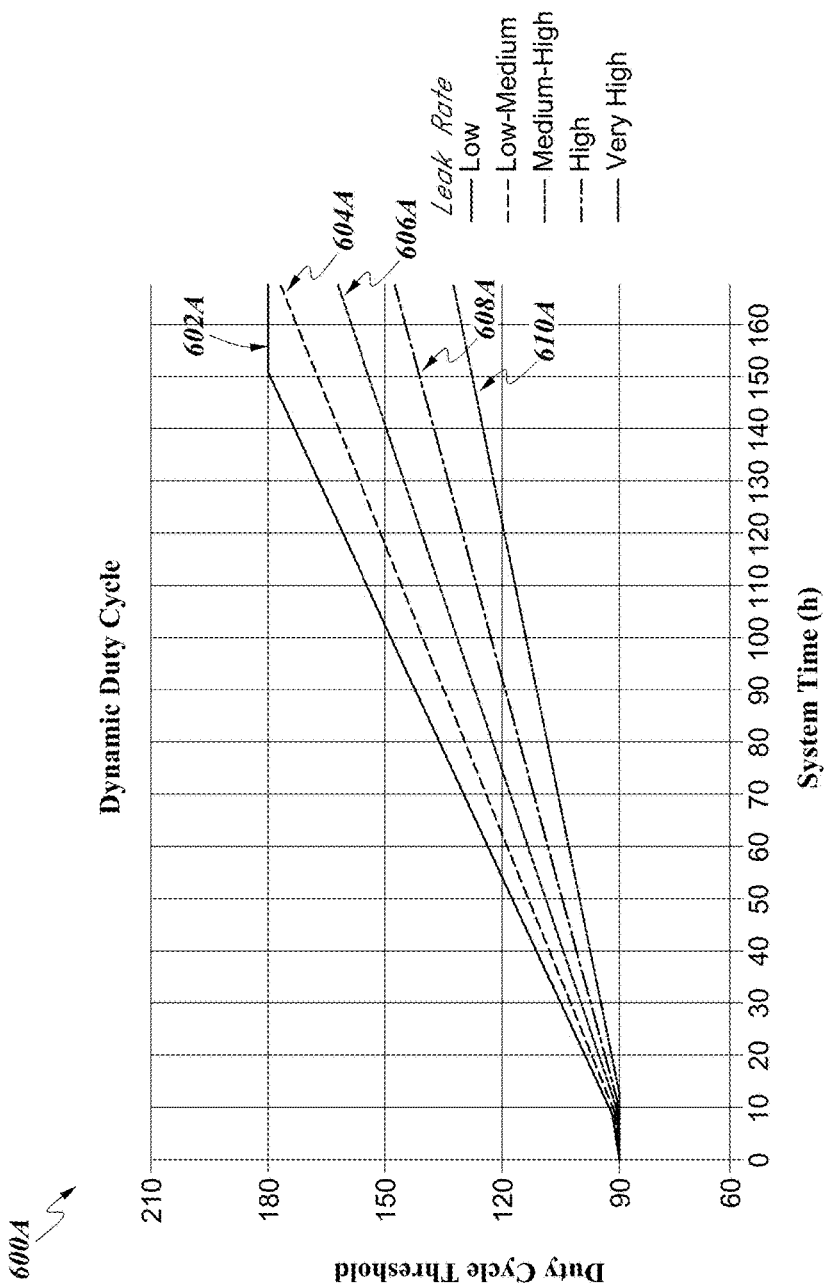
FIGS. 6A-6C illustrate a set of duty cycle threshold determinations over operational life of a pump assembly according to some embodiments.

For example, the lower bound of approximately 9% and an upper bound of approximately 18% can be selected, and β can be set to −46595 (which as explained below, provides the maximum value of the product in equation (8)). In this case, as is illustrated in FIG. 6A, $\alpha=2^{-16}$ is suitable (γ=−33255). FIG. 6A illustrates duty cycle threshold determination 600A over the operational life of the pump assembly 104 according to some embodiments. The x-axis represents operational time in hours (e.g., 168 corresponds to 7 days), and the y-axis represents the duty cycle threshold as a percentage scale (e.g., 60 corresponds to 6% and 210 corresponds to 21%). Duty cycle threshold determination 600A is illustrated in presence of a low flow leak (curve 602A), low-medium flow leak (curve 604A), medium-high flow leak (curve 606A), high flow leak (curve 608A), and very high flow leak (curve 610A). Such leak conditions can cause various levels of decline or decay in the capacity of the power source over the operational life of the pump assembly 104. For example, the capacity of the power source may remain robust over the operational life of the pump assembly in presence of a low leak. In contrast, the capacity of the power source may be rapidly drained in presence of a very high leak. Thus, in some embodiments, the separation between the curves 602A-610A should be sufficient in order to reflect the respective drains on the capacity of the power source resulting from the operation of the source of negative pressure.

As is illustrated by curve 602A, in presence of a low leak the determined duty cycle threshold reaches a desired upper bound of 18% when the pump assembly 104 nears the end of operational life (e.g., reaches approximately 150 hours of operation, which corresponds to 6.25 days). In addition, the duty cycle threshold in curve 602A starts to increase soon after initialization (e.g., approximately 10 hours into the operational life). In some embodiments, this may be due to the fact that the capacity of the power source remains high throughout the operational life of the pump assembly when a low flow leak is present. Further, as is illustrated in FIG. 6A, the lower bound of duty cycle for curves 602A-610A is a desired 9%.

Because other curves 604A, 606A, 608A, and 610A depict operation of the pump assembly 104 in presence of more severe leaks than depicted by curve 602A, the duty cycle threshold does not rise quite as rapidly for curves 604A-610A. In some embodiments, this is so because the capacity of the power source is drained more rapidly over the operational life of the pump assembly 104 as leaks become more severe (e.g., the source of negative pressure 1090 works harder when leaks with higher flow are present). For example, as is shown by curve 610A, the duty cycle threshold does not reach the upper bound of 18% when a very high leak is present in the system.

Figure 6B:
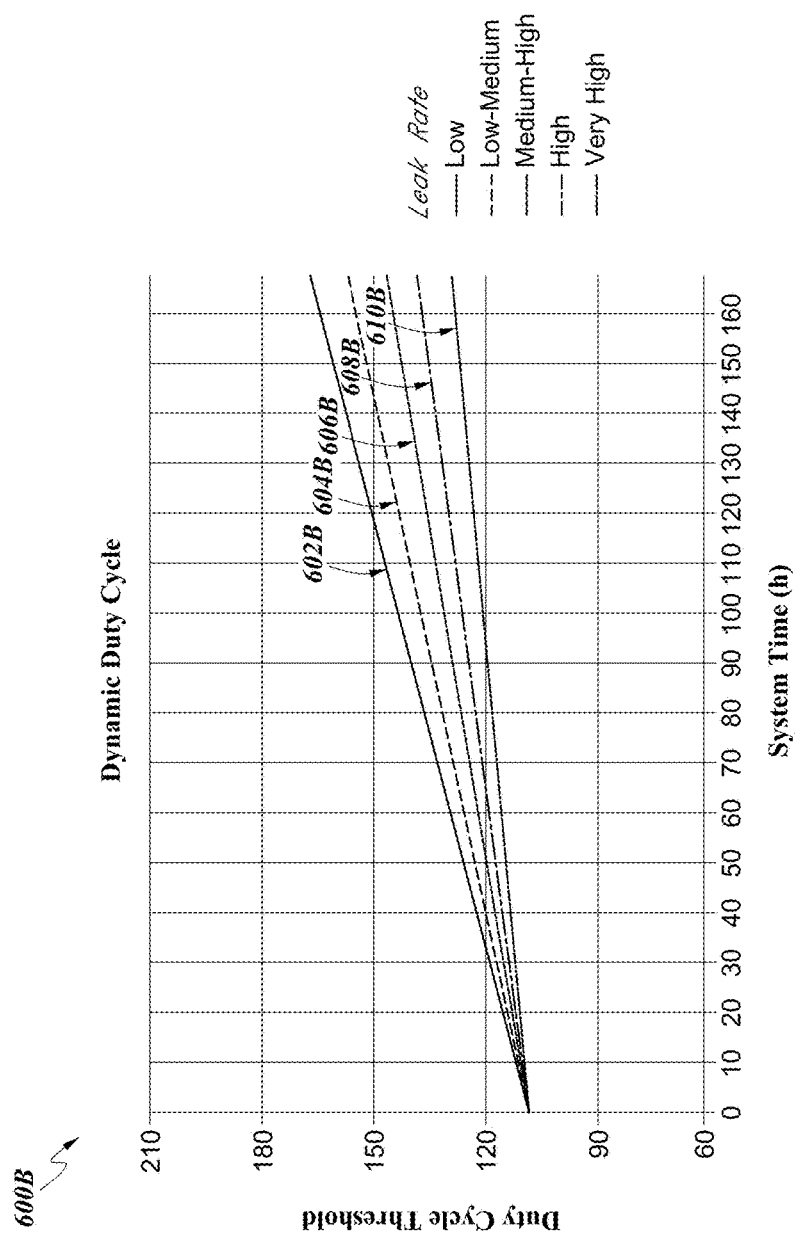

In some embodiments, $\alpha=2^{-17}$ (which is smaller than $2^{-16}$) is not suitable (for γ=−16561), as is illustrated in FIG. 6B, which depicts duty cycle threshold determination 600B over the operational life of the pump assembly 104. The x-axis represents operational time in hours (e.g., 168 corresponds to 7 days), and the y-axis represents the duty cycle threshold as a percentage scale (e.g., 60 corresponds to 6% and 210 corresponds to 21%). Duty cycle threshold determination 600B is depicted in presence of a low flow leak (curve 602B), low-medium flow leak (curve 604B), medium-high flow leak (curve 606B), high flow leak (curve 608B), and very high flow leak (curve 610B).

As is illustrated by curve 602B, in the presence of a low leak, duty cycle threshold does not reach the desired upper bound of 18% when the pump assembly 104 nears the end of operational life. The depicted upper bound is approximately 16%. In addition, the lower bound of the duty cycle threshold for curves 602B-610B is higher than the desired 9% (e.g., the lower bound is between 11% and 12%). Moreover, there is insufficient separation between the curves 602B-610B.

Figure 6C:
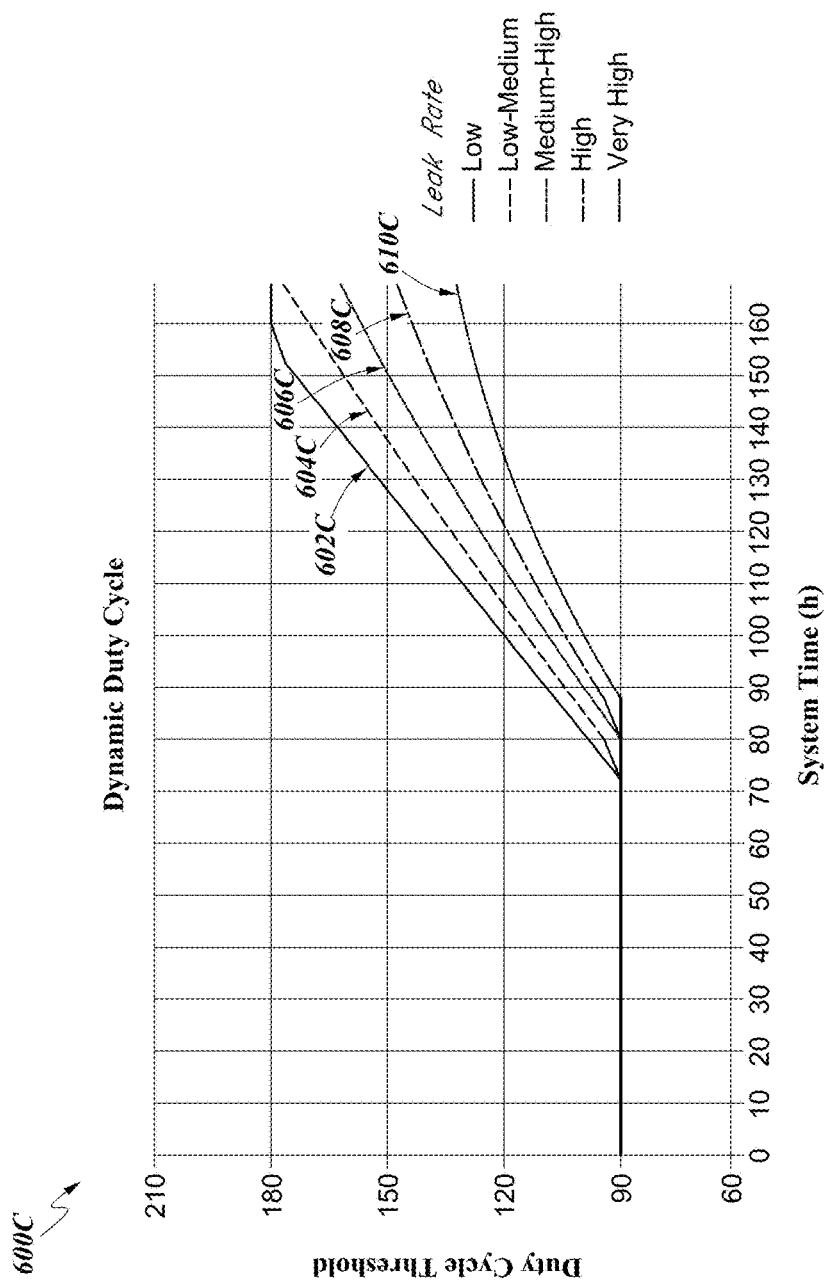

Based on the duty cycle determinations depicted in FIGS. 6A and 6B, in some embodiments, the minimum value of constant α can be selected as $2^{-16}$ (or 1/65536). In some embodiments, the maximum value of $\alpha=2^{-8}$ is suitable (β=−10, γ=−16561), as is illustrated in FIG. 6C. FIG. 6C depicts duty cycle threshold determination 600C over the operational life of the pump assembly 104 according to some embodiments. The x-axis represents operational time in hours (e.g., 168 corresponds to 7 days), and the y-axis represents the duty cycle threshold as a percentage scale (e.g., 60 corresponds to 6% and 210 corresponds to 21%). Duty cycle threshold determination 600C is depicted in presence of a low flow leak (curve 602C), low-medium flow leak (curve 604C), medium-high flow leak (curve 606C), high flow leak (curve 608C), and very high flow leak (curve 610C).

As is illustrated by curve 602C, in the presence of a low leak, duty cycle threshold reaches the desired upper bound of 18% when the pump assembly 104 nears the end of operational life (e.g., 18% is reached at approximately 160 operational hours). In addition, the lower bound of the duty cycle threshold for curves 602C-610C is the desired 9%. There is sufficient separation between the curves 602C-610C. Accordingly, in some embodiments, the values of constant α can be selected from the range $2^{-16} \leq \alpha \leq 2^{-8}$ (1/65536 ≤ α ≤ 1/256).

In some embodiments, the values of constants β and γ can be selected based at least in part on the selected value of constant α. As is illustrated in FIGS. 5A-5C, value of β and γ shift the graph horizontally or vertically. In some embodiments, values of β and γ can be selected based at least in part on desired lower and upper bounds of the duty cycle threshold. In some embodiments, the value of constant β can be selected so that it would not cause an overflow (or overflows) during calculation of the duty cycle threshold. For example, the controller 1160 (e.g., a microprocessor) can be configured to perform 32-bit signed integer calculations. In this case, the maximum value that can be represented is approximately $2^{31}$ (e.g., $2^{31}-1$), which is approximately equal to $2.15*10^9$, and the minimum values that can be represented is approximately $-2^{31}$ (e.g., $-2^{31}+1$), which is approximately equal to $-2.15*10^9$. Maximum and minimum values of constant β that avoid overflows can be calculated using equation (8) as follows:

$$(\beta+360) \times (\beta+168) = 2.15 \times 10^9 \quad (9)$$

where 360 represents the capacity of the power source in hundredth of volts (e.g., 2 Lithium batteries rated 1.8V each) and 168 represents operational time in hours (e.g., 7 days*24 hours). In order to calculate the maximum and minimum values of constant β, constant α can be set to 1 (or)$2^0$ and constant γ can be set to 0. In other embodiments, different values can be used, such as 300 for the capacity of the power source represented in hundredth of volts (e.g., 2 AA or AAA batteries rated 1.5V each), and the like. Equation (9) can be represented as:

$$\beta^2 + 528\beta + (360 \times 168) = 2.15 \times 10^9 \quad (10)$$

Solving equation (10) for roots the using quadratic formula provides the following values of constant β: −46595 or 46087. Accordingly, values of constant β can be selected from the range −46595≤β≤46087.

In some embodiments, the controller 1160 can be configured to perform 32-bit unsigned integer calculations. In this case, the maximum value that can be represented is approximately $2^{32}$ (e.g., $2^{32}-1$), and the minimum value that can be represented is 0. The maximum value can used in equation (9). In some embodiments, the controller 1160 can be configured to perform signed integer, unsigned integer, or a combination of both calculations on N-bit values, where N is an integer value, and respective maximum (or minimum) values can be used in equation (9).

In some embodiments, the following values of the constants can be used: $\alpha=2^{-17}$, $\beta=-100000$, and $\gamma=-76443$. In some embodiments, other suitable values of lower and upper bounds can be used to determine suitable range of values of one or more constants α, β, and γ. For example, the upper bound can be selected as approximately 10%, 15%, 20%, 27%, 30%, and so on. As another example, the lower bound can be selected as approximately 8% or less or more, 10% or less or more, 15% or less or more, and so on. In some embodiments, the values of lower and upper bounds can be selected based at least in part on the characteristics of the source of negative pressure (e.g., pump type) and/or capacity of the power source (e.g., battery voltage). In some embodiments, the values of constants α, β, and γ can be selected based on at least one or combination of any number of the following: a desired lower bound of the duty cycle threshold, a desired upper bound of the duty cycle threshold, characteristics of the source of negative pressure (e.g., efficiency of the pump), characteristics of the duty cycle threshold determination (such as not causing any calculation overflows), and the like. In some embodiments, the constants α, β, and γ can be selected as any suitable positive or negative value.

In some embodiments, the duty cycle threshold can be determined according to various functions of two variables, namely the capacity of the power source and operational time. For example, the duty cycle threshold can be determined according a linear function:

$$\text{DC threshold}=a^*x+b^*y+c \quad (11)$$

where a, b, and c are constants and x is a variable that corresponds to the capacity of power source and y is a variable to corresponds to the operational time. The values constants a, b, and c can be selected according to particular requirements and/or operational conditions of the system. In some embodiments, the values of the constants a, b, and c can be adjusted, such as adjusted periodically.

Figure 7:
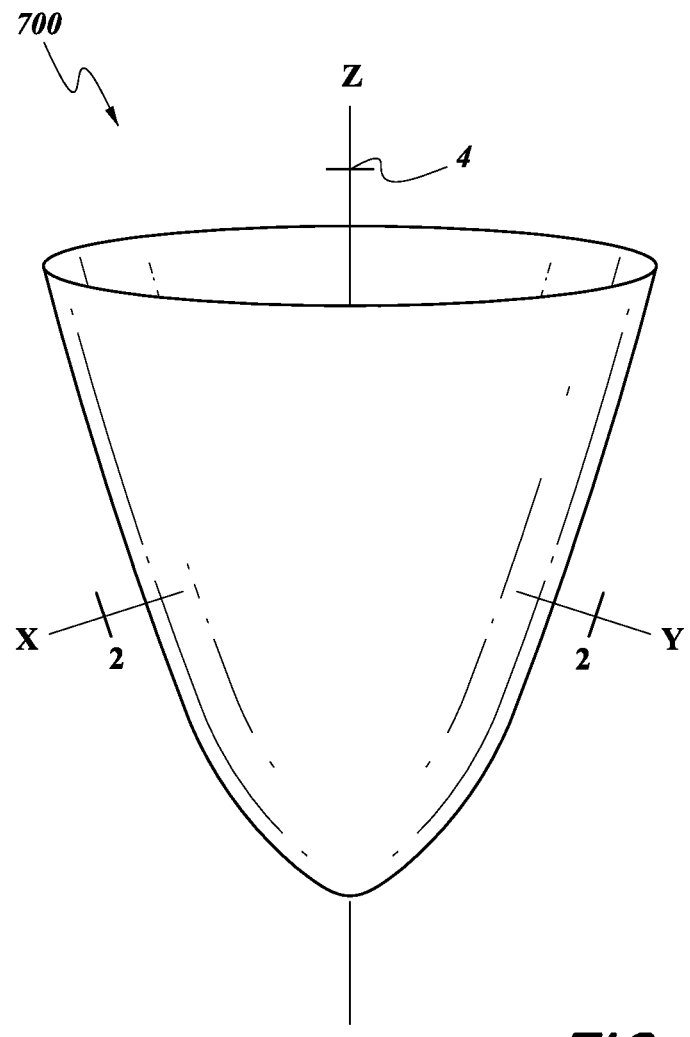
FIG. 7 illustrates a graph of a quadratic surface that can be used for determining a duty cycle threshold according to some embodiments.

As another example, the duty cycle threshold can be determined according to a quadratic function:

$$f(x, y)=a^*x^2+b^*y^2+c \quad (12)$$

where a, b, and c are constants and x is a variable that corresponds to the capacity of power source and y is a variable to corresponds to the operational time. Function of equation (12) represents a quadratic surface. For instance, FIG. 7 depicts a graph 700 of an elliptic paraboloid, which is a type of a quadratic surface. In particular, graph 700 represents the following function $$f(x, y)=2^*x^2+2^*y^2-4 \quad (13)$$

Figure 8:
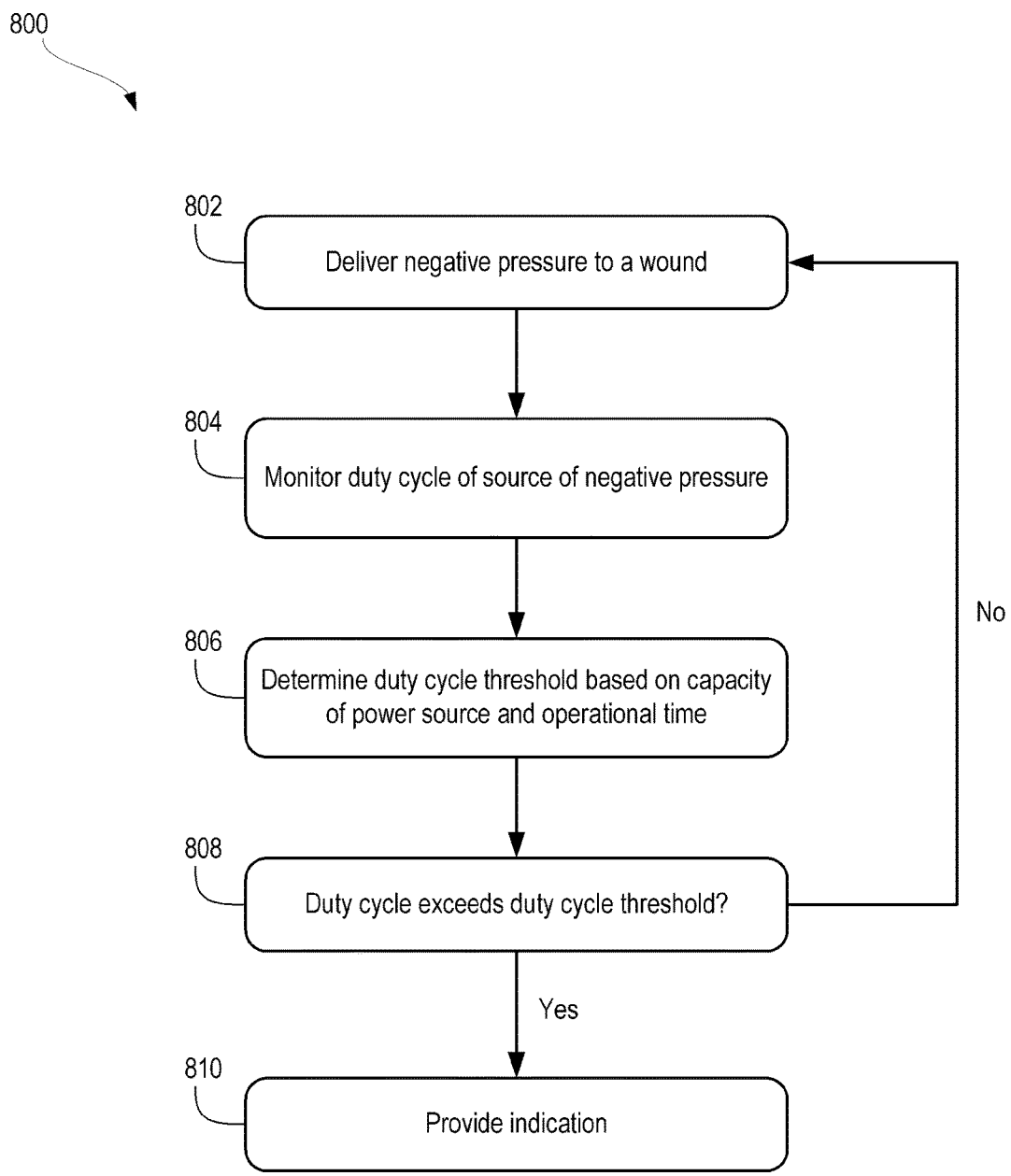
FIG. 8 is a flowchart illustrating a process of operation of the pump assembly according to some embodiments.

FIG. 8 is a flowchart illustrating a process 800 of operation of the pump assembly 104 according to some embodiments. The process 800 can be executed by the controller 1160. At block 802, the process provides therapy, such as delivers negative pressure, to a wound. This can be performed, for example, by activating the source of negative pressure 1090. In some embodiments, the process 800 activates the source of negative pressure in response to a user pressing the button 122. At block 804, the process 800 monitors the duty cycle of the source of negative pressure. This can be performed according to any embodiment described in U.S. patent application Ser. No. 13/287,959 (Exhibit A of U.S. Patent Application No. 61/613,456), published as U.S. Patent Publication No. 2012/0136325, and/or International Application No. PCT/GB2011/051745 (Exhibit B of U.S. Patent Application No. 61/613,456), published as WO 2012/038724, and such embodiments and illustrations thereof are hereby incorporated by reference in their entireties as if made part of this disclosure.

At block 806, the process 800 determines the duty cycle threshold according to any of the embodiments described above. The process 800 can periodically determine the duty cycle threshold, such as every hour, and/or monitor the duty cycle of the source of negative pressure, such as every minute. At block 808, the process 800 determines whether the duty cycle exceeds the duty cycle threshold. The process 800 can make this determination periodically (e.g., every minute). If the duty cycle is determined to not exceed the duty cycle threshold, the process 800 transitions to block 802 where it continues to deliver negative pressure to the wound. If the duty cycle is determined to exceed the duty cycle threshold, the process 800 transitions to block 810 where it provides an indication to the user. As explained above, the indication can include stopping delivery of therapy to the wound by deactivating the source of negative pressure.

As is disclosed in U.S. patent application Ser. No. 13/287,959 (Exhibit A of U.S. Patent Application No. 61/613,456), published as U.S. Patent Publication No. 2012/0136325, and/or International Application No. PCT/GB2011/051745 (Exhibit B of U.S. Patent Application No. 61/613,456), published as WO 2012/038724, in some embodiments, the process 800 can monitor a plurality of duty cycles of the source of negative pressure over a plurality time durations (such as a plurality of consecutive and equal time durations), and determine if a number of duty cycles of the plurality of duty cycles exceed the duty cycle threshold. Further, the process 800 can determine if the number of duty cycles that exceed the duty cycle threshold exceeds an overload threshold (e.g., 30). The process 800 can provide an indication when it is determined that the number of duty cycle that exceed the duty cycle threshold exceeds the overload threshold.

In some embodiments, duty cycle is determined according to equation (8) by taking into account that the capacity of the power source and operational time are different variables. In some embodiments, the capacity of the power source depletes over time as a function of the operational time. For example, the capacity of the power source (capacity) can be represented as a function of operational time (x) according to:

$$\text{capacity}=m \times x+c \quad (14)$$

Plugging equation (14) into equation (8) provides:

$$DCT=\alpha \times (x-\beta) \times (m \times x+c-\beta)+\gamma \quad (15)$$

Performing expansions and simplifications results in:

$$DCT=m\alpha x^2+c\alpha x-(1+m)\alpha\beta x-c\alpha\beta+\alpha\beta^2+\gamma \quad (16)$$

In some embodiments, the values of constants m and c are determined by approximating the duty cycle and/or the duty cycle threshold at various operating times. For example, when the apparatus 100 experiences moderate to low leak conditions, the duty cycle threshold can be set at the lower bound of approximately 9% at or near the beginning of life of the pump assembly 104. As the pump assembly approaches the end of life (e.g., 168 operational hours), the duty cycle threshold can be increased to the upper bound of approximately 18%. Further, suppose that under moderate to low leak conditions, the capacity of the power source 1130 can be approximately 3.3 V at or near the beginning of life and decay to approximately 2.58 V at or near the end of life. The values of m and c can be calculated by plugging into In some embodiments, the values of m and c can be determined using different duty cycle bounds, operational time bounds, and/or capacities of the power source than those used in the foregoing. For example, Table 1 summarizes the determined values for m and c according to different operating conditions, duty cycle values, and operational times. In addition, values of $\beta$ and $\gamma$ can be determined using different duty cycle bounds, operational times, and values of $\alpha$. For example, $\alpha$ can be set as $-2^{-8}$ (or approximately $-3.906 \times 10^{-3}$).

TABLE 1

| Operating conditions (leak rate) | Starting operating time (in hours) | Ending operating time (in hours) | Starting capacity of power source (in 1/100 V) | Ending capacity of power source (in 1/100 V) | m | c |
|---|---|---|---|---|---|---|
| low | 0 | 168 | 330 | 279 | −0.304 | 330 |
| medium-low | 0 | 168 | 330 | 258 | −0.429 | 330 |
| medium-high | 0 | 168 | 330 | 237 | −0.554 | 330 |
| high | 0 | 168 | 330 | 216 | −0.679 | 330 |
| very high | 0 | 168 | 330 | 195 | −0.804 | 330 | equation (14) the following {operational time (in hours), capacity of the power source (in 1/100 V)} pairs: (0, 330) and (168, 258).

$$330 = m*0 + c \quad (17a)$$

$$258 = 168m + c \quad (17b)$$

Solving the equations (17a) and (17b) provides c=330 and m=−72/168 (or approximately −0.429).

In some embodiments, the values of constants $\alpha$, $\beta$, and $\gamma$ are determined as follows. As explained above, it can be advantageous to select $\alpha$ to be a multiple of two. The following {operational time (in hours), duty cycle threshold (in % multiplied by 10)} pairs can be plugged into the equation (16): ($x_1$=0, $y_1$=90) and ($x_2$=168, $y_2$=180). This provides:

$$y_1 = m\alpha x_1^2 + c\alpha x_1 - (1+m)\alpha\beta x_1 - c\alpha\beta + \alpha\beta^2 + \gamma \quad (18a)$$

$$y_2 = m\alpha x_2^2 + c\alpha x_2 - (1+m)\alpha\beta x_2 - c\alpha\beta + \alpha\beta^2 + \gamma \quad (18b)$$

Solving the equations (18a) and (18b) for provides:

$$\beta = \frac{(y_1 - y_2) - m\alpha(x_1^2 - x_2^2)}{(x_1 - x_2)\alpha(-1 - m)} \quad (19)$$

Once $\beta$ has been determined by plugging values for m (e.g., −72/168) and for $\alpha$, $\gamma$ can be determined according to:

$$\gamma = y - m\alpha x^2 - c\alpha x + (1+m)\alpha\beta x + c\alpha\beta - \alpha\beta^2 \quad (20)$$

For example, selecting $\alpha = -2^{-8}$ (or approximately $-3.906 \times 10^{-3}$) and using ($x_1$=0, $y_1$=90) and ($x_2$=168, $y_2$=180) provides $\beta \approx 691.5$ and $\gamma \approx 1066.5$.

In some embodiments, the capacity of the power source is related to the operational time according to a linear relationship that is different from equation (14) or according to a non-linear relationship. In various embodiments, operational time can be represented as a function of the capacity of the power source. In certain embodiments, the values of m and c are determined using different assumptions about the operating conditions and duty cycle values at different operational times, such as during a high leak condition, no leak condition, and the like.

Figure 9:
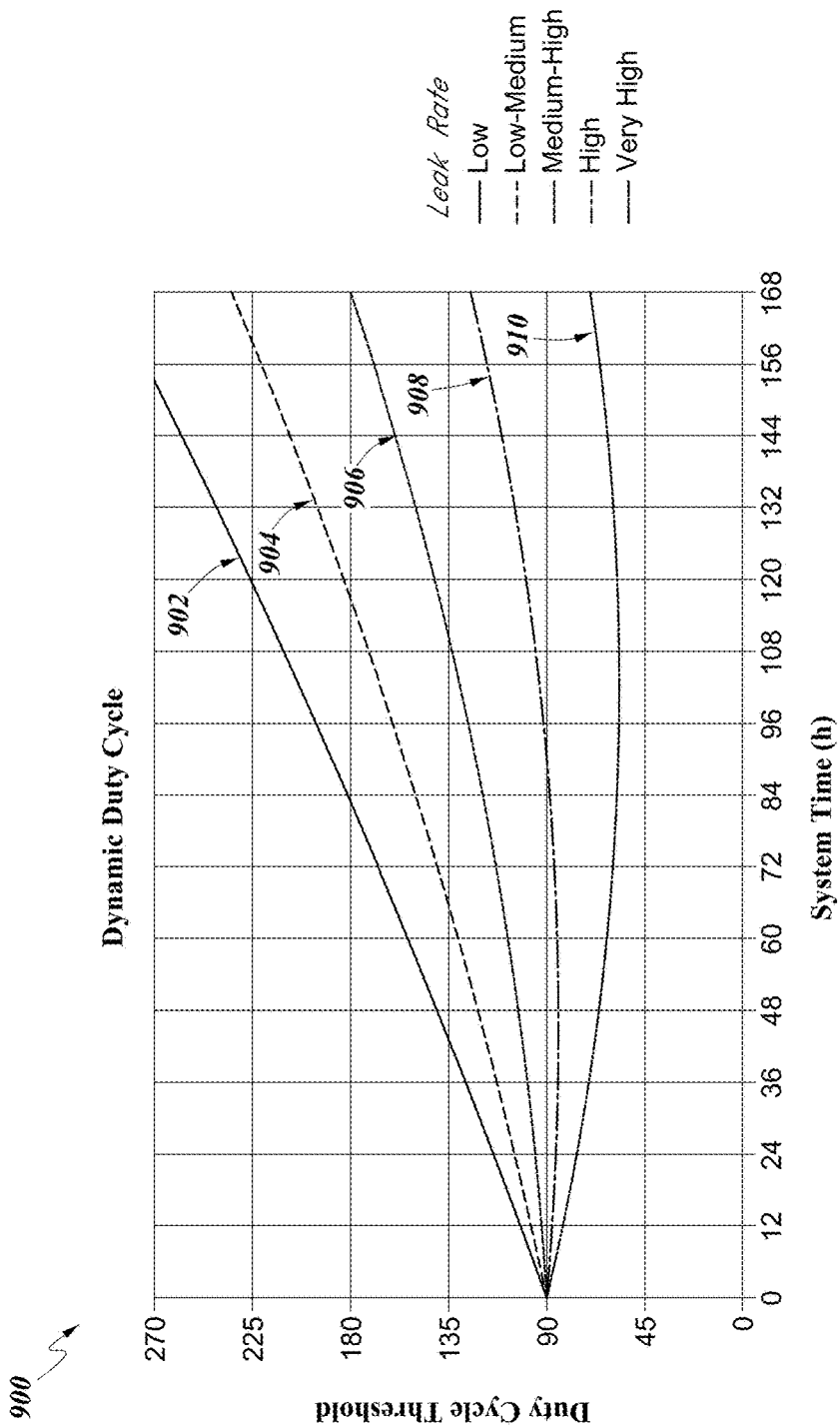
FIG. 9 illustrates another set of duty cycle threshold determinations over operational life of a pump assembly according to some embodiments.

FIG. 9 illustrates duty cycle threshold determinations 900 over the operational life of the pump assembly 104 according to some embodiments. As in FIGS. 6A-6C, the x-axis represents operational time in hours (e.g., 168 corresponds to 7 days), and the y-axis represents the duty cycle threshold as a percentage scale (e.g., 90 corresponds to 9%). Duty cycle threshold determination 900 is illustrated in presence of a low flow leak (curve 902), low-medium flow leak (curve 904), medium-high flow leak (curve 906), high flow leak (curve 908), and very high flow leak (curve 910). As is illustrated, at or near the beginning of life of the pump assembly 104, the duty cycle threshold is set to 9%. In presence of a low leak (curve 902), the determined duty cycle threshold increases over the operational life of the pump assembly 104, reaching and exceeding 27% because the capacity of the power source remains robust. In contrast, as the curves 904, 906, 908, and 910 depict the operation of the pump assembly 104 in the presence of more severe leaks than that depicted by curve 902, the duty cycle threshold does not rise quite as rapidly for curves 904-910. In some embodiments, this is so because the capacity of the power source is drained more rapidly over the operational life of the pump assembly 104 as leaks become more severe (e.g., the source of negative pressure 1090 works harder when leaks with higher flow are present). For example, in the presence of a very high leak (curve 910), the determined duty cycle threshold decreases over the operational life of the pump assembly 104, remaining below 9% starting value of the duty cycle threshold throughout the operational life of the pump assembly 104.

The curves illustrated in FIG. 9 can be determined according to equations (16) through (20). For example, $\alpha$ can be set as $-2^{-8}$ (or approximately $-3.906 \times 10^{-3}$). As another example, curve 904 corresponding to low-medium leak conditions can be generated by using $\beta \approx 691.5$ and $\gamma \approx 1066.5$. In other embodiments, $\alpha$ can be set to any suitable value that is a power of two or not a power of two, and the values of $\beta$ and $\gamma$ can be determined as explained above. The transitions illustrated by curves 902-910 are smooth over the lifetime of the pump assembly 104. The curves 902-910 maintain sufficient separation between the respective leak rates.

Figure 10:
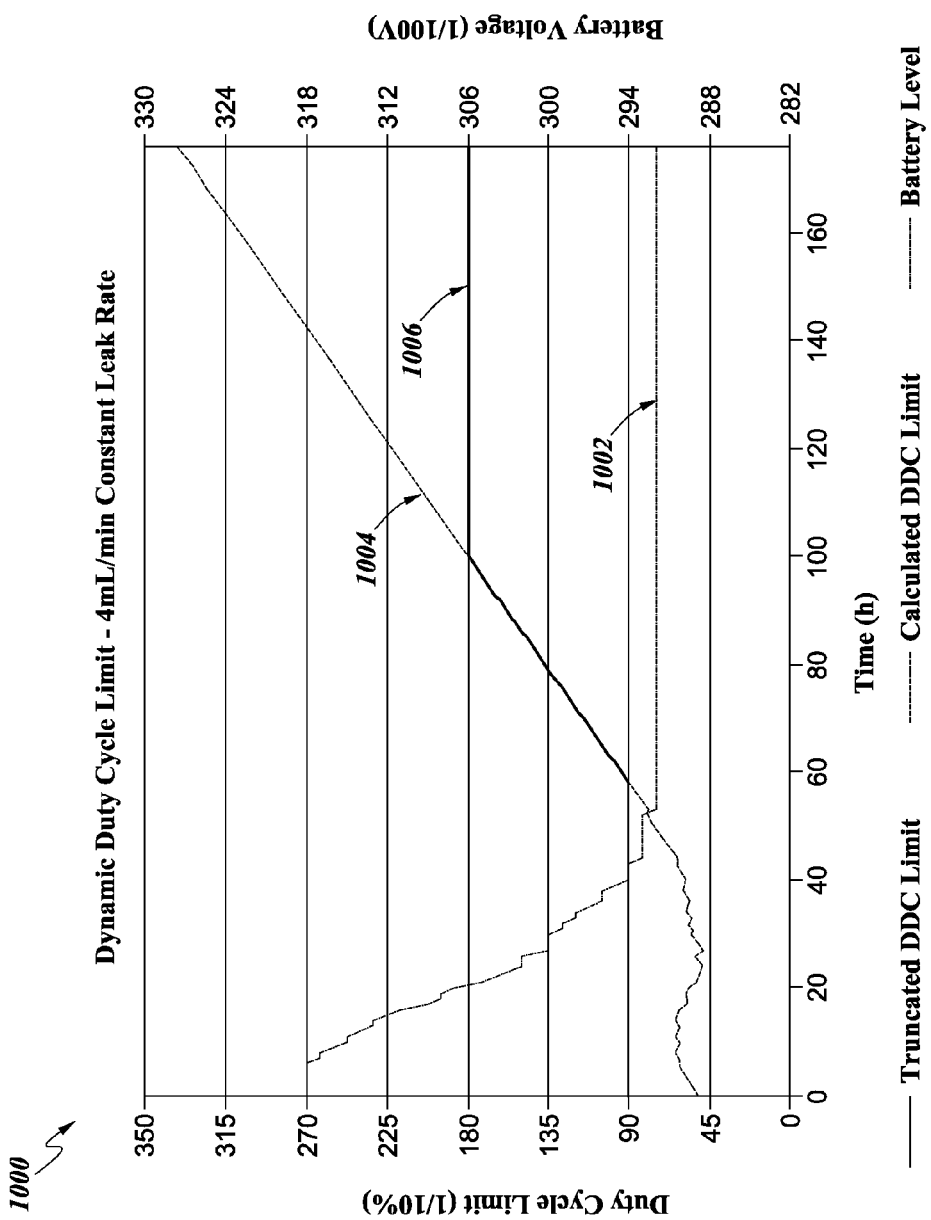
FIG. 10 illustrates yet another duty cycle threshold determination over operational life of a pump assembly according to some embodiments.

FIG. 10 illustrates duty cycle threshold determination 1000 over the operational life of a pump assembly according to some embodiments. The plot 1000 has been generated by applying a PICO pump assembly to a wound model, while maintaining a constant air leak (e.g., 4 mL/min) Data for generating the plot 1000 was collected in real-time while the PICO pump assembly was operating on the wound model. The the x-axis represents operational time in hours (e.g., 168 corresponds to 7 days), the y-axis on the left side represents the duty cycle threshold as a percentage scale (e.g., 90 corresponds to 9%), and the y-axis on the right side represents the capacity of the power source in $1/100$ of a volt (e.g., 282 corresponds to 2.82 V).

Curve 1002 illustrates the capacity of the power source over the operational lifetime of the PICO pump assembly. As is illustrated, at or near the beginning of life, the capacity of the power source is approximately 3.18 V. The capacity of the power source decays to about 2.92 V after about 53 hours of operation and remains at that level until the end of life is reached. The duty cycle threshold illustrated by curve 1004 starts at about 5.3% at or near the beginning of life and rises to about 32.5% at or near the end of life. Truncated duty cycle threshold, which is the duty cycle threshold clipped to remain in the range between a lower bound of 9% and an upper bound of 18% is illustrated by curve 1006.

Data collected during the experiment conduced with the PICO pump assembly and shown in FIG. 10 illustrates that, in some embodiments, performing the dynamic duty cycle threshold determination according to the present disclosure allows the pump assembly to deliver optimal or substantially optimal negative pressure therapy in the presence of leaks. By monitoring the capacity of the power source over the operational lifetime of the pump assembly, duty cycle threshold can be increased or decreased based on the operating conditions. This can result in an improved efficiency, achieving an appropriate balance between an uninterrupted delivery of therapy and/or avoidance inconveniencing a user, conserving power, limiting vibrational noise, and/or patient comfort.

Power Source Capacity Determination

In some embodiments, the capacity of the power source 1130 can be determined by measuring an instantaneous capacity of the power source (e.g., voltage or current). In some embodiments, the capacity of the power source can be determined by the controller 1160. For example, the instantaneous capacity can be measured periodically, such as every n seconds, where n can be selected as any suitable integer or non-integer value (e.g., 60 seconds). However, the instantaneous capacity can fluctuate, which can lead to an unreliable or distorted measure of the power source capacity. For example, when the source of negative pressure 1090 is active, the instantaneous voltage (or current) reading can drop due to power being drawn from the power source 1130 by the source of negative pressure 1090. That is, instantaneous voltage (or current) can "sag" during the pump down 1622.

In some embodiments, the capacity of the power source 1130 is monitored and a new minimum capacity is recorded periodically. For example, the controller 1160 can monitor the capacity of the power source every n seconds and record a new minimum capacity if a currently measured capacity falls below a previously recorded minimum capacity. N can be selected as any suitable integer or non-integer value, such as 60 seconds. The capacity of the power source 1130 can be measured, for example, via measuring voltage or current provided by the power source. However, during periods of high activity, such as when the source of negative pressure 1090 is running, the capacity of the power source 1130 may drop due to power being drawn. For example, when there is a leak in the system, the source of negative pressure 1090 is allowed to run in order to attempt to achieve a desired level of negative pressure in the wound cavity. Recording minimum capacity during such periods of high activity can result in a distorted measure of the capacity of the power source 1130. In certain embodiments, a new maximum capacity is recorded.

In some embodiments, the capacity of the power source 1130 is monitored, for example, periodically. Multiple measurements of the power source capacity taken during different times can be filtered to remove distortions associated with, for example, the activity of the source of negative pressure 1090. Any suitable analog or digital filtering can be performed, such as infinite impulse response filtering or finite impulse response filtering. In various embodiments, low pass filtering is performed to determine an average or mean value of the power source capacity. However, because filtering can be computationally intensive, it may not be desirable to perform such calculations in order, for example, to conserve the capacity of the power source. In certain embodiments, one or more of low pass filtering, high pass filtering, band pass filtering, band stop filtering, or the like can be performed.

In some embodiments, the capacity of the power source 1130 is determined by monitoring and recording the capacity at the beginning and end of the pump down 1622. For example, a first measure of the capacity of the power source can be made when the source of negative pressure 1090 is activated, such as when position 1608 is reached. The first measure of capacity can be made immediately after the source of negative pressure 1090 has been activated or soon thereafter. A second measure of the capacity of the power source can be made when the source of negative pressure 1090 is deactivated, such as when position 1610 is reached. The second measure of capacity can be made immediately after the source of negative pressure 1090 has been deactivated or soon thereafter. In certain embodiments, the capacity of the power source 1130 is determined based on the first and second measures of the capacity of the power source. In some embodiments, a mean or average value of the first and second measures of the capacity of the power source is used as the power source capacity. The first and second measured of capacity of the power source can be combined in any suitable way. In various embodiments, additional measures of the capacity of the power source are made during pump down 1622, and these additional measures are combined with the first and second measure of the capacity. For example, a mean, median, or the like value of the first, second, and additional measures of the capacity can be determined as used as the capacity of the power source.

Other Variations

In some embodiments, the pump assembly 104 can be configured to directly monitor the flow rate of fluid (e.g., air and/or liquid) over a period of time (e.g., 45 seconds or less or more, 60 seconds or less or more, 90 seconds or less or more, 2 minutes or less or more, 3 minutes or less or more, 4 minutes or less or more, etc). This can be accomplished by using any suitable flow meter, for instance, a mass flow meter. The pump assembly 104 can be configured to determine a flow rate threshold based on the monitored flow rate. The pump assembly 104 can be further configured to determine and adjust the flow rate threshold based at least in part on the operational time and/or capacity of the power source. This can be performed alternatively or in addition to monitoring the duty cycle and determining and adjusting the duty cycle threshold.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, integers, characteristics, compounds, chemical moieties or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes, such as the process illustrated in FIG. 8, may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Furthermore, the features and attributes of the specific embodiments disclosed above may be combined in different ways to form additional embodiments, all of which fall within the scope of the present disclosure.

Although the present disclosure provides certain preferred embodiments and applications, other embodiments that are apparent to those of ordinary skill in the art, including embodiments which do not provide all of the features and advantages set forth herein, are also within the scope of this disclosure. Certain embodiments of the invention are encompassed in the appended claims.

What is claimed is:

1. An apparatus for applying negative pressure to a wound, the apparatus comprising:
   a negative pressure source configured to be fluidically coupled to a wound dressing via a fluid flow path;
   a power source configured to supply power to the negative pressure source; and
   a controller configured to:
      monitor a duty cycle of the negative pressure source, a time elapsed from an initial activation of the negative pressure source, and a remaining capacity of the power source, the time elapsed from the initial activation being monitored independently from the remaining capacity of the power source;
      adjust a duty cycle threshold based at least in part on the remaining capacity of the power source and the time elapsed from the initial activation; and
      when a leak is present in the fluid flow path, operate the negative pressure source based at least in part on a comparison of the duty cycle and the duty cycle threshold.

2. The apparatus of claim 1, wherein the controller is further configured to:
   activate the negative pressure source; and
   provide an indication in response to determining that the duty cycle has exceeded the duty cycle threshold.

3. The apparatus of claim 2, wherein controller is configured to provide the indication by deactivating the negative pressure source.

4. The apparatus of claim 1, wherein the duty cycle reflects an amount of time the negative pressure source is active over a period of time.

5. The apparatus of claim 1, wherein the controller is configured to monitor the time elapsed from the initial activation by updating a counter based at least on the time elapsed from the initial activation.

6. The apparatus of claim 1, wherein the controller is further configured to disable activation of the negative pressure source when the time elapsed from the initial activation reaches a lifetime threshold.

7. The apparatus of claim 6, wherein the lifetime threshold comprises at least 7 days.

8. The apparatus of claim 1, wherein the controller is configured to monitor the remaining capacity of the power source based on at least one of a voltage of the power source or a current of the power source.

9. The apparatus of claim 1, wherein the duty cycle threshold is bounded between lower and upper bounds, and the lower and upper and bounds are, respectively, about 35% and about 70%.

10. The apparatus of claim 1, wherein the controller is further configured to periodically determine the duty cycle threshold.

11. The apparatus of claim 1, wherein the controller is further configured to determine the duty cycle threshold hourly.

12. The apparatus of claim 1, wherein the controller is further configured to:
    determine a first capacity of the power source when the negative pressure source is active;
    determine a second capacity of the power source when the negative pressure source is inactive; and
    determine the capacity of the power source based at least in part on the first and second capacities of the power source.

13. The apparatus of claim 12, wherein the controller is configured to determine the capacity of the power source based on averaging of the first and second capacities of the power source.

14. The apparatus of claim 1, wherein the negative pressure source comprises a voice coil pump.

15. A method for operating a negative pressure apparatus comprising a negative pressure source and a power source, the method comprising:
    delivering negative pressure from the negative pressure source to a wound dressing via a fluid flow path;
    supplying power to the negative pressure source with the power source;

monitoring a duty cycle of the negative pressure source, a time elapsed from initial activation of the negative pressure source, and a remaining capacity of the power source, the time elapsed from the initial activation being monitored independently from the remaining capacity of the power source;

adjusting a duty cycle threshold based at least in part on the remaining capacity of the power source and the time elapsed from the initial activation; and when a leak is present in the fluid flow path, operating the negative pressure source based at least in part on a comparison of the duty cycle and the duty cycle threshold.

16. The method of claim 15, further comprising:
activating the negative pressure source; and
providing an indication in response to determining that the duty cycle has exceeded the duty cycle threshold.

17. The method of claim 16, wherein said providing the indication comprises deactivating the negative pressure source.

18. The method of claim 15, wherein the duty cycle reflects an amount of time the negative pressure source is active over a period of time.

19. The method of claim 15, wherein said monitoring the time elapsed from the initial activation comprises updating a counter based at least on the time elapsed from the initial activation.

20. The method of claim 15, further comprising disabling activation of the negative pressure source when the time reaches a lifetime threshold.

21. The method of claim 20, wherein the lifetime threshold comprises at least 7 days.

22. The method of claim 15, wherein said monitoring the remaining capacity of the power source comprises monitoring the remaining capacity of the power source based on at least one of a voltage of the power source or a current of the power source.

23. The method of claim 15, further comprising bounding the duty cycle threshold between lower and upper bounds, the lower and upper bounds being, respectively, about 9% and about 18%.

24. The method of claim 15, further comprising periodically determining the duty cycle threshold.

25. The method of claim 24, wherein the duty cycle threshold is determined hourly.

26. The method of claim 15, wherein said monitoring the remaining capacity of the power source comprises:
determining a first capacity of the power source when the negative pressure source is active;
determining a second capacity of the power source when the negative pressure source is inactive; and
determining the capacity of the power source based at least in part on the first and second capacities of the power source.

27. The method of claim 26, wherein said determining capacity of the power source comprises determining the capacity of the power source using averaging of the first and second capacities of the power source.

28. The method of claim 15, wherein the negative pressure source comprises a voice coil pump.

* * * * *

UNITED STATES PATENT AND TRADEMARK OFFICE
CERTIFICATE OF CORRECTION

PATENT NO. : 9,901,664 B2  Page 1 of 1
APPLICATION NO. : 14/386322
DATED : February 27, 2018
INVENTOR(S) : Ben Alan Askem It is certified that error appears in the above-identified patent and that said Letters Patent is hereby corrected as shown below:

In the Specification

Column 1, Line 13, change "it" to --in--.

Column 3, Line 25, change "inHg" to --mmHg--.

Column 5, Line 1, change "X %)," to --X%),--.

Column 9, Line 1, change "DRAM." to --DRAM,--.

Column 13, Line 62 (approx.), change "powersource" to --power source--.

Column 16, Line 51 (approx.), change "βthat" to --β that--.

Column 16, Line 59 (approx.), change "(or)2⁰" to --(or 2⁰)--.

Column 17, Line 40 (approx.), change "a *x" to --a*x--.

Column 19, Line 36, change "αto" to --α to--.

Column 19, Line 47-49, change "$\beta = \frac{(y_1 - y_2) - m\alpha(x_1^2 - x_2^2)}{(x_1 - x_2)\sigma(-1 - m)}$" to --$\beta = \frac{(y_1 - y_2) - m\alpha(x_1^2 - x_2^2)}{(x_1 - x_2)\alpha(-1 - m)}$--.

Column 21, Line 5, change "mL/min)" to --mL/min).--.

In the Claims

Column 24, Line 38, in Claim 9, change "lower and upper and bounds" to --lower and upper bounds--.

Signed and Sealed this
Twenty-second Day of January, 2019

Andrei Iancu
*Director of the United States Patent and Trademark Office*